US010238790B2

(12) United States Patent
Toro et al.

(10) Patent No.: US 10,238,790 B2
(45) Date of Patent: Mar. 26, 2019

(54) SYRINGE HOLDER

(71) Applicant: CareFusion 2200, Inc., San Diego, CA (US)

(72) Inventors: Daniel Toro, Chula Vista, CA (US); Santiago Roman Dodge, Santee, CA (US); Dana Frizzell, Murietta, CA (US); Scott Belliveau, San Diego, CA (US); Corey Michael Magers, Oceanside, CA (US); Lee Good, San Diego, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 0 days.

(21) Appl. No.: 14/641,228

(22) Filed: Mar. 6, 2015

(65) Prior Publication Data
US 2016/0256621 A1    Sep. 8, 2016

(51) Int. Cl.
| | | |
|---|---|---|
| *A61M 5/14* | (2006.01) |
| *F16M 13/02* | (2006.01) |
| *F16B 2/06* | (2006.01) |
| *A61M 5/00* | (2006.01) |
| *A61M 5/145* | (2006.01) |
| *F16C 29/02* | (2006.01) |

(52) U.S. Cl.
CPC .............. *A61M 5/14* (2013.01); *A61M 5/008* (2013.01); *A61M 5/1458* (2013.01); *F16B 2/06* (2013.01); *F16M 13/02* (2013.01); *F16C 29/02* (2013.01); *F16C 2316/10* (2013.01)

(58) Field of Classification Search
CPC .......... A61M 2209/082; A61M 5/1415; A61M 5/1417; A61M 1/652; A61M 2209/08; F16M 11/22; A61G 2203/78; F16B 2/10; H05K 7/14; A47B 96/06; Y10T 24/3443
USPC .............. 604/257; 210/646, 541; 108/144.11
See application file for complete search history.

(56) References Cited

U.S. PATENT DOCUMENTS

| | | | | |
|---|---|---|---|---|
| 1,216,531 | A * | 2/1917 | Wolf ....................... | B60R 11/00 24/338 |
| 1,307,011 | A * | 6/1919 | Kohn ....................... | F16M 5/00 220/DIG. 8 |
| 2,156,025 | A * | 4/1939 | Paul ..................... | A24F 19/0092 211/107 |
| 2,269,790 | A * | 1/1942 | Sherrill ..................... | B01L 9/50 24/132 R |

(Continued)

FOREIGN PATENT DOCUMENTS

| | | | | |
|---|---|---|---|---|
| WO | WO 2014/151508 A1 | * | 9/2014 | .............. A61M 1/36 |
| WO | WO 2014151508 A1 | * | 9/2014 | .......... A61M 5/1415 |

*Primary Examiner* — Nathan R Price
*Assistant Examiner* — John A Doubrava
(74) *Attorney, Agent, or Firm* — Morgan, Lewis & Bockius LLP

(57) ABSTRACT

A syringe adapter for holding various sizes of syringes. A syringe includes a tip, a barrel, a plunger, a flange, and a syringe axis extending from the tip to the plunger. An example syringe holder attaches to a fluid delivery system and includes a syringe clamp. The syringe holder holds a syringe stationary in the syringe clamp. The syringe clamp is offset from the fluid delivery system such that the syringe, or connections to the syringe, does not interfere with other components of the fluid delivery system. The syringe holder may include a support bar, which the syringe clamp can slide along. Alternatively, the syringe clamp may be rotatable.

24 Claims, 22 Drawing Sheets

(56) References Cited

U.S. PATENT DOCUMENTS

| | | | | |
|---|---|---|---|---|
| 2,638,301 | A * | 5/1953 | Smith | B01L 9/50 24/274 R |
| 2,915,096 | A * | 12/1959 | Mooney | B25B 5/103 269/157 |
| 4,038,982 | A * | 8/1977 | Burke | A61M 5/1689 128/DIG. 13 |
| D251,440 | S * | 3/1979 | Inoue | D24/169 |
| 4,211,380 | A * | 7/1980 | Lillegard | A61G 7/0503 24/328 |
| 5,015,226 | A * | 5/1991 | Polaschegg | A61M 1/3672 604/505 |
| 5,770,064 | A * | 6/1998 | Jonsson | A61M 1/16 210/232 |
| 6,089,518 | A * | 7/2000 | Nilsson | A61G 12/002 248/317 |
| 6,277,277 | B1 * | 8/2001 | Jacobi | A61M 1/16 210/232 |
| 6,592,551 | B1 * | 7/2003 | Cobb | A61M 5/1456 128/DIG. 1 |
| 6,883,766 | B1 * | 4/2005 | Ziaylek | A62B 9/04 248/154 |
| 7,976,515 | B2 * | 7/2011 | Murphy | A61M 5/16809 604/250 |
| 8,844,556 | B2 * | 9/2014 | Honma | A61M 5/36 137/197 |
| 8,864,657 | B2 * | 10/2014 | Tydlaska | A61B 1/00052 600/186 |
| 8,926,562 | B2 * | 1/2015 | Fathallah | A61M 5/1418 248/74.1 |
| 9,022,981 | B2 * | 5/2015 | Oesterreich | A61M 1/16 604/131 |
| 9,186,454 | B2 * | 11/2015 | Lundqvist | A61M 5/1415 |
| D746,470 | S * | 12/2015 | Kobayashi | D24/128 |
| 9,283,145 | B2 * | 3/2016 | Beiriger | A61M 1/342 |
| 9,291,305 | B2 * | 3/2016 | Brehm | F16M 13/022 |
| 9,295,778 | B2 * | 3/2016 | Kamen | G06F 19/3406 |
| 9,579,438 | B2 * | 2/2017 | Haecker | A61M 1/16 |
| 2003/0135152 | A1 * | 7/2003 | Kollar | A61M 1/3621 604/35 |
| 2005/0042570 | A1 * | 2/2005 | Fischer | A61C 19/004 433/29 |
| 2010/0213151 | A1 * | 8/2010 | Theesfeld | A47B 57/06 211/151 |
| 2014/0046296 | A1 * | 2/2014 | Clarke | A61M 5/1456 604/507 |
| 2014/0188076 | A1 * | 7/2014 | Kamen | A61M 5/1408 604/506 |
| 2015/0041419 | A1 * | 2/2015 | Hasegawa | A61M 5/1413 211/85.13 |
| 2015/0157791 | A1 * | 6/2015 | Desch | A61M 5/1408 604/506 |
| 2016/0022894 | A1 * | 1/2016 | Jensen | A61M 5/1415 210/646 |

* cited by examiner

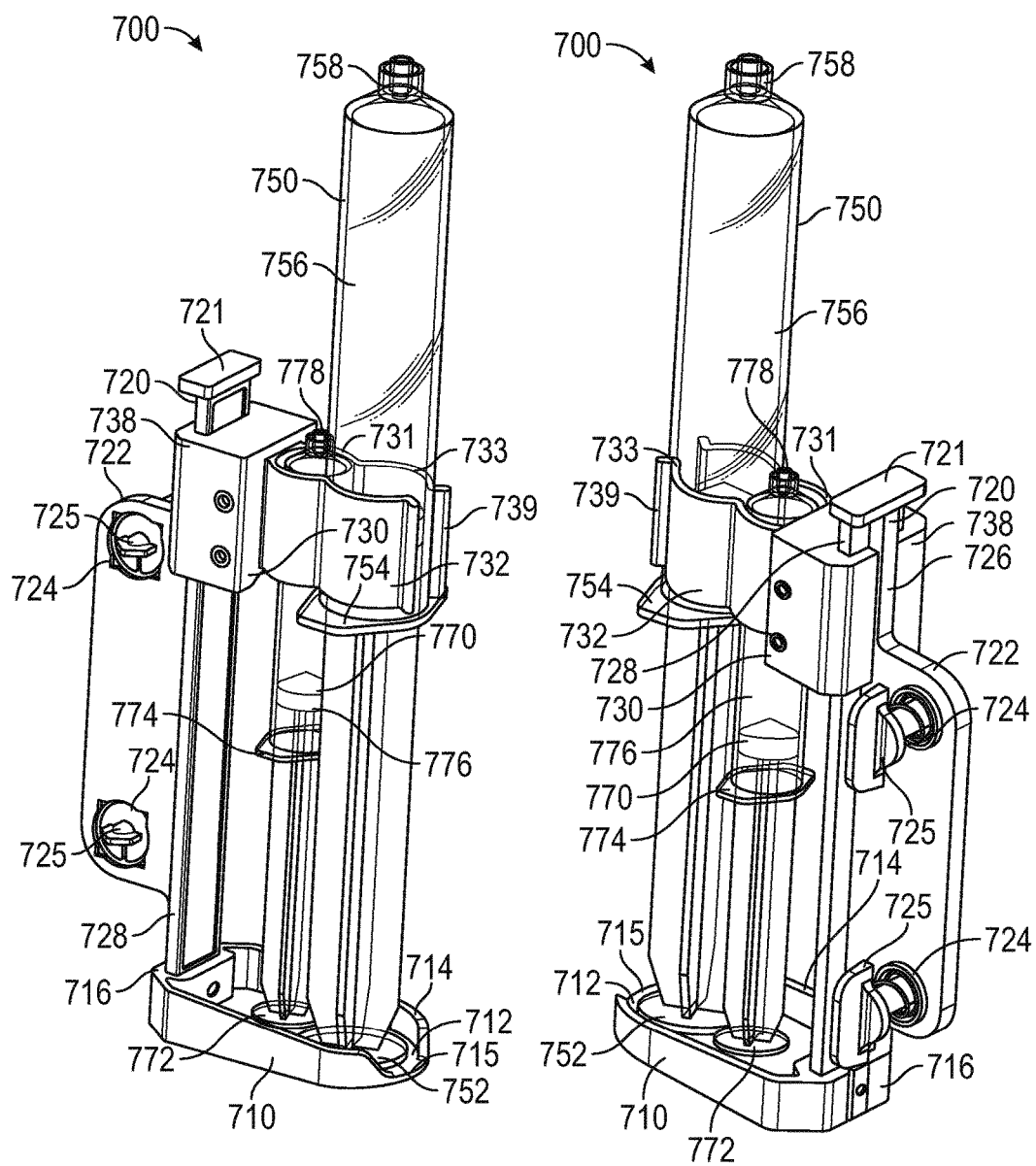

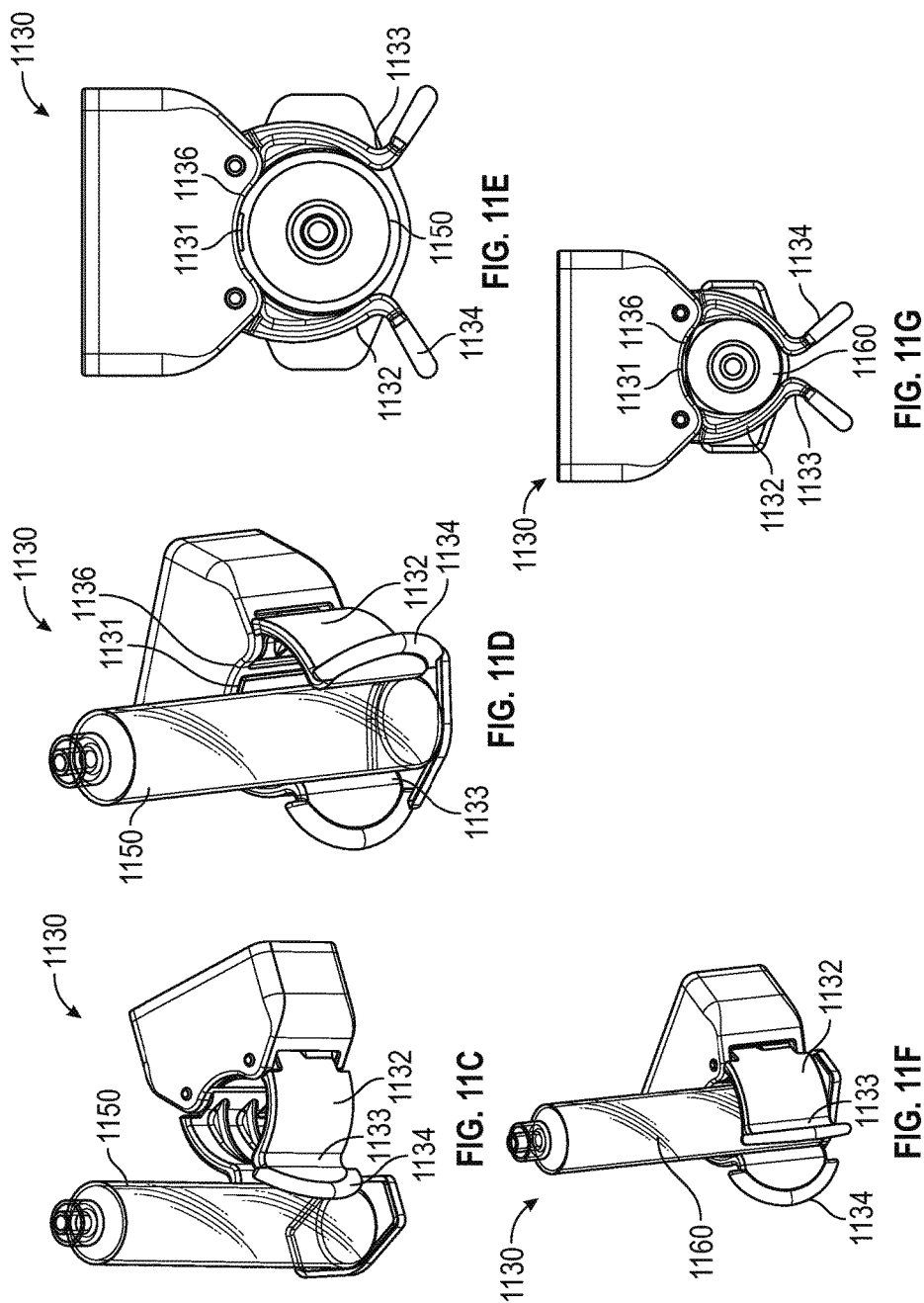

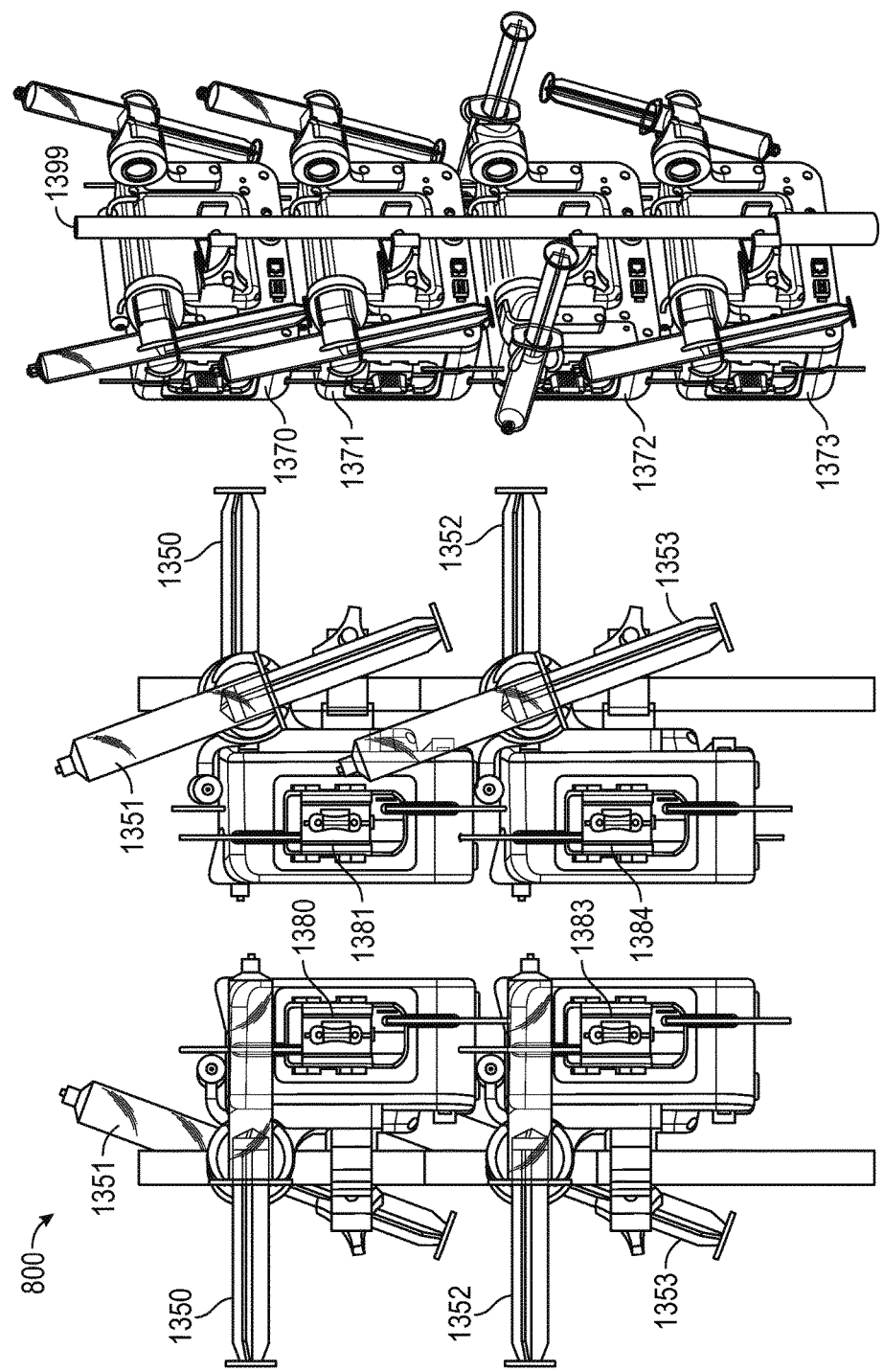

SYRINGE HOLDER

TECHNICAL FIELD

The present disclosure generally relates to a syringe holder, and more particularly to a syringe holder used with an infusion device.

BACKGROUND

Infusion devices and related fluid delivery systems may be used to safely and accurately deliver infusions to patients. Infusion devices may deliver medications, nutrients, and other fluids to a patient. Infusion devices may administer fluids in specific amounts and rates and over periods of time that may be difficult or impractical for a nurse to manually administer. Infusion devices may further be able to control boluses. Infusion devices can be broadly classified by their pumping mechanism, either pulling fluid from a reservoir or pushing fluid from a reservoir. The former includes large volume pumps that pump fluid from a bag or other reservoir through pumping mechanisms, including, for example, a peristaltic pump acting on a fluid line, or a reciprocating piston pump that acts to draw and expel fluid from a defined space. The latter includes syringe pumps that typically secure a syringe barrel in a fixed position and push or "drive" a syringe plunder into a barrel at a controlled rate to expel the fluid. In a typical hospital setting, both syringe pumps and large volume pumps are desirable as medication is loaded into both bags and syringes for administration to patients.

SUMMARY

In an effort to reduce the number of different devices needed by a hospital (or another care center), it would be desirable to provide systems, mechanisms, and methods that would allow fluids to be pulled from a syringe that could be attached to infusion devices. Aspects of the subject technology relate to syringe holders for use with infusion devices and methods of using the same. In accordance with aspects, a syringe holder for housing a syringe comprising a tip, a barrel, a plunger, a flange, and a syringe axis extending from the tip to the plunger is disclosed. The syringe holder comprises a plunger guard comprising a seating surface configured to hold the plunger stationary, a support bar connected to the plunger guard and configured to extend parallel to the syringe axis, and a syringe clamp connected to the support bar and configured to hold the barrel. The syringe clamp is configured to slide along the support bar from a home position towards the plunger guard, and the home position is near an end of the support bar distal from the plunger guard.

In implementations, the syringe clamp comprises a syringe flange slot configured to mate with a flange of the syringe. In implementations, the support bar extends vertically above the plunger guard. In implementations, the syringe clamp is configured to move down from a home position towards the plunger guard. In implementations, the plunger guard and the syringe clamp are configured to hold the syringe such that a fluid within the syringe is extracted against gravity. In implementations, the syringe clamp is configured to freely slide along the support bar. In implementations, the band comprises an elastomeric band. In implementations, the band comprises a ratchet locking mechanism. In implementations, the band defines a first chamber and a second chamber. In implementations, a radius of the first chamber is different from a radius of the second chamber. In implementations, the syringe clamp further comprises a tab configured to release the syringe clamp, wherein the tab is extended outward when the syringe clamp is in a home position, and the tab is recessed when the syringe clamp moves away from the home position. In implementations, the syringe holder comprises a syringe assist mechanism configured to assist in movement of the syringe clamp away from a home position. In implementations, the syringe assist mechanism comprises a rack-and-pinion gear with a spring mechanism along the support bar. In implementations, the syringe assist mechanism comprises a weight. In implementations, the syringe holder comprises a flexure configured to hold the syringe clamp in a home position. In implementations, the syringe holder comprises a guard wall configured to at least partially encircle the syringe. In implementations, the syringe holder comprises a sensor configured to detect whether the syringe clamp is in a home position.

In accordance with aspects, a fluid delivery system is disclosed. The fluid delivery system comprises a fluid delivery device comprising a main body, a plunger guard comprising a seating surface, a support bar connected to the plunger guard. The support bar comprises a support tab attached to the main body. The fluid delivery system also comprises a syringe clamp connected to the support bar. The syringe clamp is configured to slide along the support bar from a home position towards the plunger guard. The home position is near an end of the support bar distal from the plunger guard.

In implementations, the fluid delivery system comprises a pump configured to extract fluid from a syringe against gravity.

In accordance with aspects, a fluid delivery system is disclosed. The fluid delivery system comprises a fluid delivery device comprising a main body. The main body comprises a side wall and a back side, a pump embedded in the side wall. The fluid delivery system also comprises a syringe holder extending laterally from the back side. The syringe holder comprises a plunger guard comprising a seating surface, and a support bar connected to and extending vertically above the plunger guard. The support bar comprises a support tab attached to the back side of the main body. The syringe holder also comprises a syringe clamp connected to the support bar. The syringe clamp is configured to slide along the support bar from a home position towards the plunger guard. The home position is near an end of the support bar distal from the plunger guard.

In accordance with aspects, a syringe holder is disclosed. The syringe holder comprises a housing configured to enclose a syringe plunger. The syringe holder comprises a spring mechanism disposed within the housing and configured to apply a force to the syringe plunger, and a follower connected to the spring mechanism and configured to contact the syringe plunger.

In implementations, the syringe holder comprises a feature configured to retract the follower against the spring mechanism when the housing is open. In implementations, the feature is configured to be released when the housing is closed.

In accordance with aspects, a syringe holder is disclosed. The syringe holder comprises a base comprising an attachment portion and a pivot portion defining a pivot axis. The syringe holder comprises a syringe clamp configured to hold a syringe transversely to the pivot axis. The syringe holder also comprises a swivel configured to couple with the base and the syringe clamp. The swivel is configured to provide relative rotational movement between the base and the syringe clamp about the pivot axis.

In implementations, the syringe clamp is configured to hold the syringe perpendicular to the pivot axis. In implementations, the syringe clamp comprises a syringe clamp arm configured to move between an open position and a closed position. In implementations, the syringe clamp arm is configured to move to the closed position by a spring mechanism. In implementations, the syringe clamp arm comprises an outward-projecting portion. In implementations, the syringe clamp further comprises a pad. In implementations, the swivel is configured to freely rotate. In implementations, the swivel is configured to rotate between a first angle about the pivot axis and a second angle about the pivot axis. In implementations, the pivot portion comprises a first detent mechanism configured to lock the swivel at a first detent angle about the pivot axis. In implementations, the first detent mechanism comprises an audible indicator.

In accordance with aspects, a fluid delivery system is disclosed. The fluid delivery system comprises a fluid delivery device comprising a main body. The fluid delivery system comprises a base comprising an attachment portion connected to the main body and a pivot portion defining a pivot axis. The fluid delivery system comprises a syringe clamp configured to hold a syringe transversely to the pivot axis. The fluid delivery system also comprises a swivel configured to couple with the base and the syringe clamp. The swivel is configured to provide relative rotational movement between the base and the syringe clamp about the pivot axis.

In implementations, the syringe clamp comprises a pair of syringe clamp arms configured to move together in a closed position and move apart in an open position. In implementations, each of the pair of syringe clamp arms is configured to move to the closed position by a respective spring mechanism. In implementations, the pivot portion comprises a detent mechanism configured to lock the swivel at one of a plurality of detent angles about the pivot axis. In implementations, the syringe clamp is configured to extend away from the main body. In implementations, the syringe clamp is configured to extend away from the main body such that a plane of rotation of the syringe clamp is offset from the main body.

In accordance with aspects, a fluid delivery system is disclosed. The fluid delivery system comprises a first fluid delivery device comprising a first main body. The fluid delivery system comprises a first base comprising a first attachment portion connected to the first main body and a first pivot portion defining a first pivot axis. The fluid delivery system comprises a first syringe clamp configured to hold a first syringe transversely to the first pivot axis, and a first swivel configured to couple with the first base and the first syringe clamp. The first swivel is configured to provide relative rotational movement between the first base and the first syringe clamp about the first pivot axis. The fluid delivery system also comprises a second fluid delivery device comprising a second main body. The fluid delivery system comprises a second base comprising a second attachment portion connected to the second main body and a second pivot portion defining a second pivot axis. The fluid delivery system comprises a second syringe clamp configured to hold a second syringe transversely to the second pivot axis. The fluid delivery system comprises a second swivel configured to couple with the second base and the second syringe clamp. The second swivel is configured to provide relative rotational movement between the second base and the second syringe clamp about the second pivot axis.

In implementations, the first pivot portion comprises a first detent mechanism configured to lock the first swivel at one of a first plurality of detent angles about the first pivot axis, and the second pivot portion comprises a second detent mechanism configured to lock the second swivel at one of a second plurality of detent angles about the second pivot axis. In implementations, when the first syringe is held by the first syringe clamp at one of the first plurality of detent angles and when the second syringe is held by the second syringe clamp at one of the second plurality of detent angles, an offset space is defined between the first syringe and the second syringe. In implementations, the second main body comprises a bumper configured to offset the first main body from the second main body.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 7A illustrates a side view of a third example syringe holder holding a large syringe and a small syringe, in accordance with aspects of the present disclosure.

FIG. 7B illustrates an alternate side view of the syringe holder of FIG. 7A.

FIG. 11C shows the syringe clamp of FIG. 11A with a syringe, in accordance with aspects of the present disclosure.

FIG. 11D shows the syringe clamp of FIG. 11C with the syringe partially installed, in accordance with aspects of the present disclosure.

FIG. 11E shows the syringe clamp of FIG. 11C with the syringe fully installed, in accordance with aspects of the present disclosure.

FIG. 11F shows the syringe clamp of FIG. 11C with another syringe installed, in accordance with aspects of the present disclosure.

FIG. 11G shows a top-down view of the syringe clamp and the another syringe of FIG. 11F, in accordance with aspects of the present disclosure.

FIG. 13C shows a side view of the fluid delivery system of FIG. 13A, in accordance with aspects of the present disclosure.

FIG. 13D shows an opposite side view of the fluid delivery system of FIG. 13A, in accordance with aspects of the present disclosure.

FIG. 13E shows the fluid delivery system of FIG. 13A with additional fluid delivery devices, in accordance with aspects of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components may be shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1A:
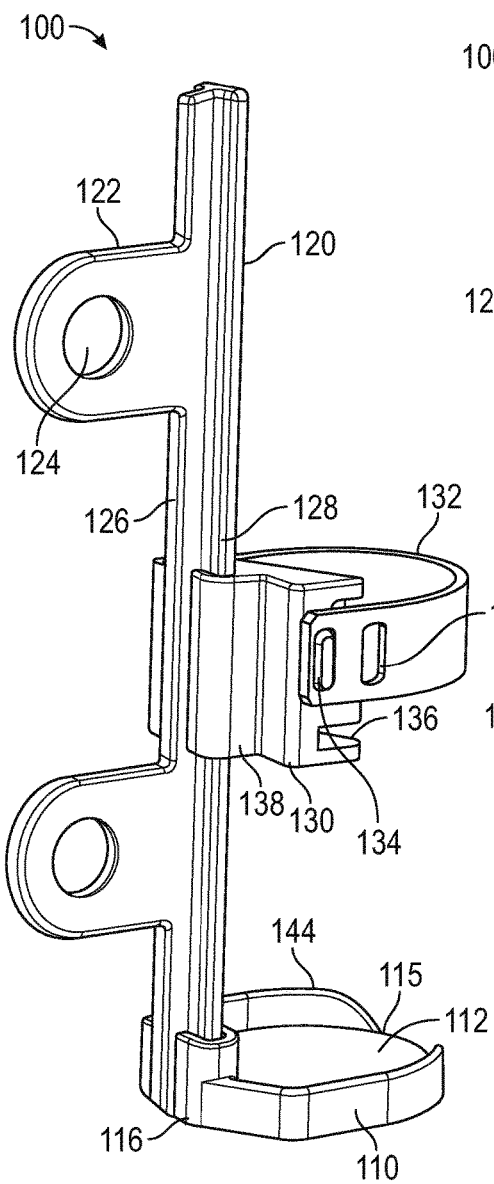
FIG. 1A illustrates a back-side view of an example of a syringe holder, in accordance with aspects of the present disclosure.
Figure 1B:
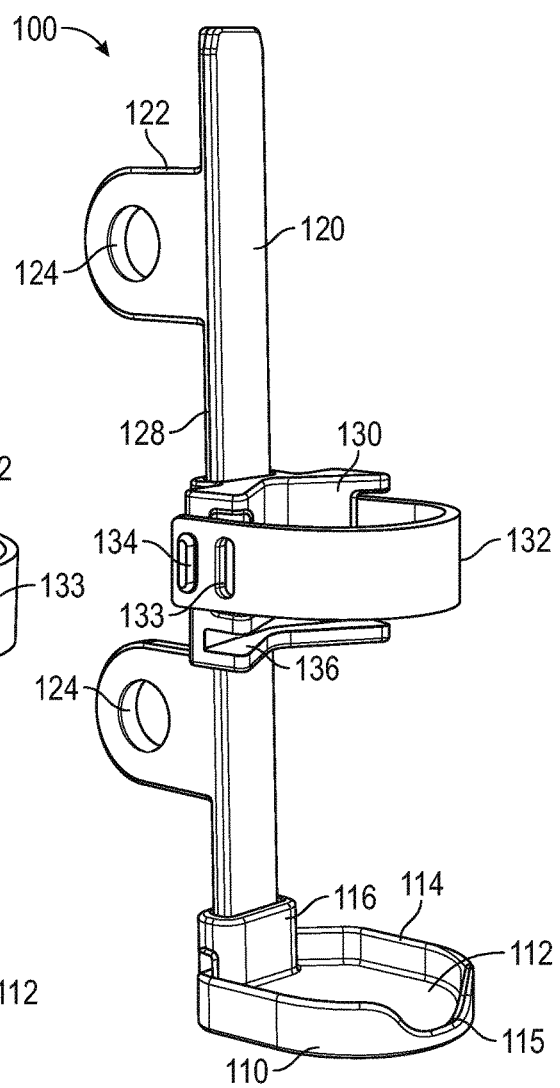
FIG. 1B illustrates a frontal view of the example syringe holder of FIG. 1A, in accordance with aspects of the present disclosure.

FIGS. 1A-1F illustrate an exemplary syringe holder 100. FIG. 1A shows a back-side view of the syringe holder 100 and FIG. 1B shows a frontal view of the syringe holder 100. The syringe holder 100 comprises a stationary plunger guard 110, support bar 120, and syringe clamp 130. The plunger guard 110 comprises a seating surface 112, a guard wall 114, a gap 115, and a base connector 116. The support bar 120 comprises a support tab 122, a spine 126, and a support surface 128. The support tab 122 defines a hole 124. The syringe clamp 130 comprises a band 132, a latch bar 134, a syringe flange slot 136, and a sliding portion 138. The band 132 defines a latch hole 133.

The syringe holder 100 is configured to hold syringes of various sizes without interfering with other devices in the system. For example, in FIG. 1C, the syringe holder 100 holds a large syringe 150, in FIG. 1D, the syringe holder 100 holds a small syringe 160, and in FIGS. 1E and 1F, the syringe holder 100 holds a micro syringe 170. The large syringe 150 comprises a plunger 152, a flange 154, a barrel 156, and a tip 158. The small syringe 160 comprises a plunger 162, a flange 164, a barrel 166, and a tip 168. The micro syringe 170 comprises a plunger 172, a flange 174, a barrel 176, and a tip 178.

The large syringe 150 may be, for example, a 60 cc syringe. The small syringe 160 may be, for example, a 5 cc syringe. The micro syringe 170 may be, for example, a 1 cc syringe. The syringe sizes are not limiting and may vary within the scope of the present disclosure. However, the large syringe 150 corresponds to syringes larger than the small syringe 160 and micro syringe 170, such that the large syringe 150 is larger (e.g., having larger components) and holds more volume than the small syringe 160 and the micro syringe 170. The large syringe 150 may hold significantly more volume, such as 10 times greater volume. The circumferences of the respective barrels 156, 166, and 176 vary according to the volume held.

Figures 1C, 1D:
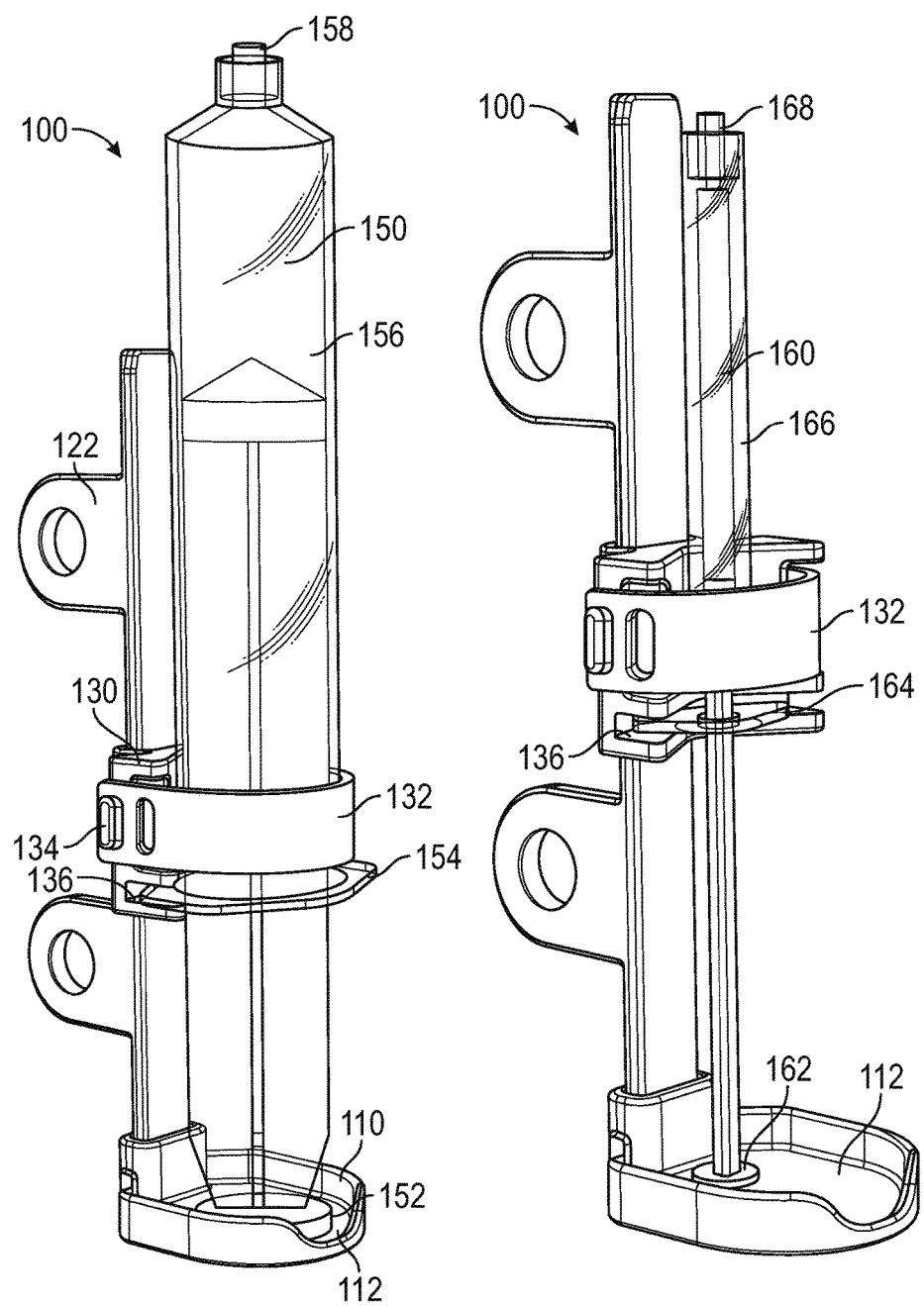
FIG. 1C illustrates a frontal view of the example syringe holder of FIG. 1A holding a large syringe, in accordance with aspects of the present disclosure.
FIG. 1D illustrates a frontal view of the example syringe holder of FIG. 1A holding a micro syringe, in accordance with aspects of the present disclosure.
Figures 1E, 1F:
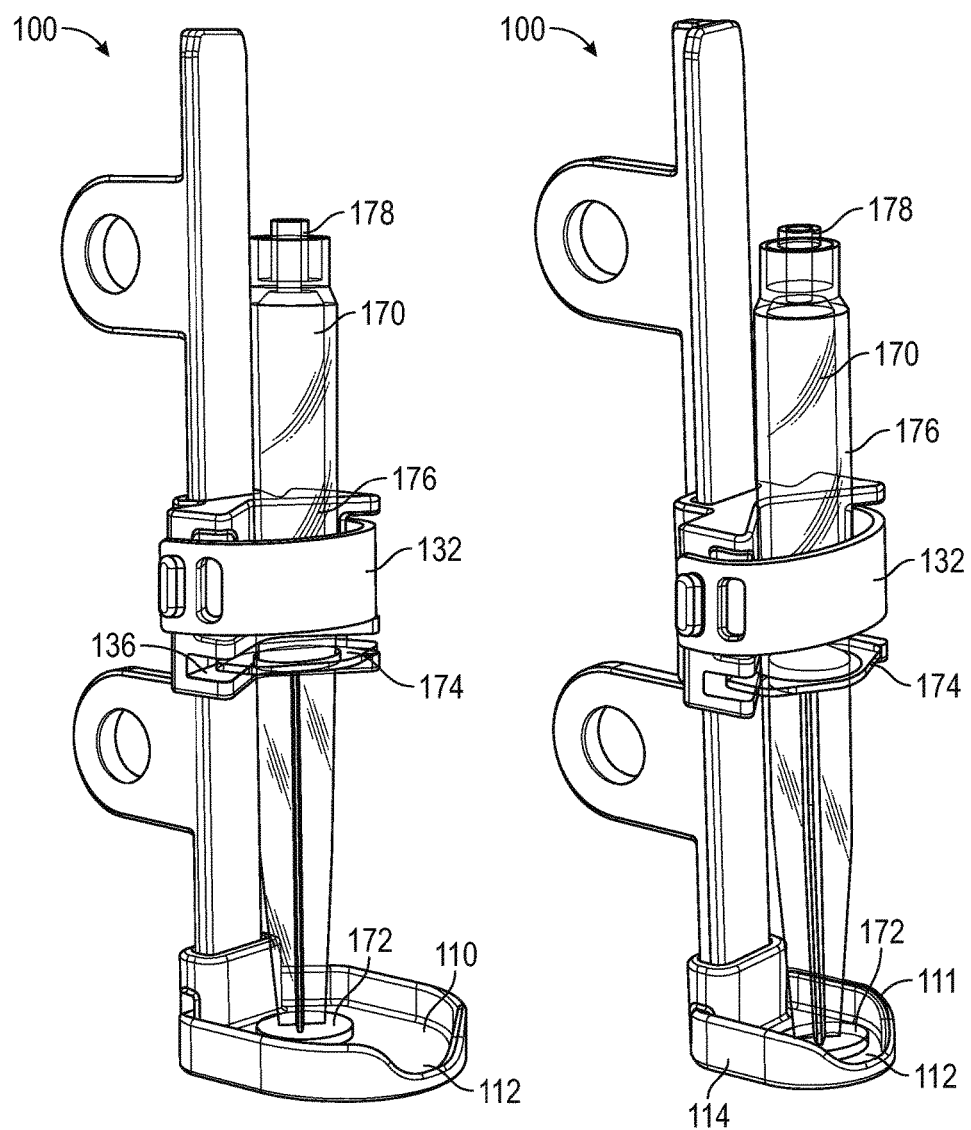
FIG. 1E illustrates a frontal view of the example syringe holder of FIG. 1A holding a small syringe, in accordance with aspects of the present disclosure.
FIG. 1F illustrates a frontal view of a modified example syringe holder of FIG. 1A holding the small syringe, in accordance with aspects of the present disclosure.

The plunger guard 110 is configured to provide a stable surface, such as the seating surface 112, to hold a syringe. By holding the plunger stable and stationary, the plunger guard 110 may help prevent or control boluses. As seen in FIG. 1C, the seating surface 112 holds the plunger 152 stationary, in FIG. 1D, the seating surface 112 holds the plunger 162 stationary, in FIG. 1E, the seating surface 112 holds the plunger 172 stationary. FIG. 1F shows another implementation of a plunger guard 111 having the seating surface 112 and guard wall 114. The plunger guard 111 may be smaller than the plunger guard 110 and is configured to hold smaller syringes, such as the micro syringe 170 or the small syringe 160, which are smaller than the large syringe 150. The plungers 172 and 162 are smaller than the plunger 162 and may not require a large seating surface 112.

The seating surface 112 may be made of a non-slip material to further prevent a plunger from shifting. The guard wall 114 is configured to prevent the plunger from shifting out of the seating surface 112. The guard wall 114 partially encircles the syringe. The gap 115 in the guard wall 114 may allow for easier insertion and extraction of the plunger from the plunger guard 110. In certain implementations, the guard wall 114 may extend higher, for example beyond a midpoint of the support bar 120, to provide greater protection to the syringe (e.g., from bumps), and to further prevent the syringe from falling out or other accidental removal.

The base connector 116 of the plunger guard 110 is configured to connect to the support bar 120. The base connector 116 may be shaped complementary to the support bar 120 such that the base connector 116 mates with the support bar 120 to provide a stable connection that does not allow the support bar 120 to move, and the base connector 116 to be removed from the support bar 120. The support bar 120 is vertically oriented such that it generally extends along an axis parallel to a syringe axis, which extends from a tip to a plunger of a syringe when the syringe is held in the syringe holder 100.

In FIGS. 1A-1F, the support bar 120 comprises the spine 126 meeting the support surface 128 in a "T" shape, or T-bar. (See FIG. 5B for a top-down view showing the "T" shape). The T-bar structure may provide sturdy and rigid (e.g., non-bending) support without requiring significant amounts of material, or a thick support bar 120. However, in other implementations, the support bar 120 may comprise any other structure capable of remaining rigid. The spine 126 further comprises one or more support tabs 122, which defines the hole 124. The support tab 122 and the hole 124 are configured to connect the syringe holder 100 to another device, such as a fluid delivery device as will be further discussed below. Although the support bar 120 comprises the support tab 122 and the hole 124 for attachment, in other implementations other attachment mechanisms may be used. For example, the support tab 122 may comprise protrusions for snapping into a fluid delivery device, or may use magnets for attachment.

The support surface 128 further forms a set of rails, as the support surface 128 extends laterally from the spine 126. The sliding portion 138 of the syringe clamp 130 is configured to wrap around or mate with the support surface 128 such that the syringe clamp 130 can slide up and down the support bar 120. When the syringe clamp 130 is in a home position (see syringe clamp 230 in FIG. 2A), which may be when the syringe clamp 130 is at an end of the support bar 120 distal from the plunger guard 110, the syringe clamp 130 may be configured to lock into the home position to prevent sliding. The syringe clamp 130 may be locked into the home position by a release tab (see release tab 231 in FIG. 2A) in conjunction with a flexure. For instance, when no syringe is inserted, the syringe clamp 130 remains in the home position for easier syringe loading. The release tab may be incorporated with or adjacent the band 132 (see FIG. 2A). In certain implementations, a sensor, such as a Hall effect sensor, may detect when the syringe clamp 130 is locked in the home position. In certain implementations, the sensor may further detect when a syringe is loaded and the syringe clamp 130 is locked in the home position, and may signal a warning to alert a user that the syringe clamp 130 is locked in the home position.

The syringe clamp 130 comprises the band 132 and the latch bar 134. The band 132 may be detachably connected to the sliding portion 138 on at least one side of the sliding portion 138 by mating with the latch bar 134. The band 132 includes one or more latch holes 133. The band 132 connects to the latch bar 134 by fitting the latch hole 133 around the latch bar 134. The one or more latch holes 133 may be placed in the band 132 in order to adjust a circumference needed to securely hold syringes of various sizes. For example, the syringe clamp 130 can securely hold the barrel 156 in FIG. 1C, the barrel 166 in FIG. 1D, and the barrel 176 in FIGS. 1E and 1F. The band 132 may be hinged one a side opposite the latch bar 134 (see band 232 in FIG. 2A and band 532 in FIG. 5A). In certain implementations, the band 132 may have latch holes 133 on both ends of the band 132. The band 132 may be made of an elastomeric material to snugly hold the syringe. In certain implementations, the band 132 and latch bar 134 may be implemented with a ratchet device which locks at notches forming decreasing circumferences, which may be released by a release lever. In certain implementations, the band 132 may be connected to a spring configured to hold the band 132 closed against the sliding portion 138.

The syringe clamp 130 also comprises a syringe flange slot 136 configured to receive a syringe flange. For example, the syringe flange slot 136 receives the flange 154 in FIG. 1C, the flange 164 in FIG. 1D, and the flange 174 in FIGS. 1E and 1F. The syringe flange slot 136, in conjunction with the band 132, securely attaches the syringe clamp 130 to a syringe. More specifically, the syringe clamp 130 securely attaches with a barrel of a syringe and is configured to move along with the barrel, such as the barrel 156 in FIG. 1C, the barrel 166 in FIG. 1D, and the barrel 176 in FIGS. 1E and 1F.

A syringe is vertically oriented upside down in the syringe holder 100. For example in FIG. 1C, the plunger 152 is upside down such that the plunger 152 is at the bottom and the tip 158 is at the top. Fluid within the large syringe 150 is extracted through the tip 158, against gravity. Similarly, the small syringe 160 is vertically oriented upside down in FIG. 1D, and the micro syringe 170 is vertically oriented upside down in FIGS. 1E and 1F. In FIG. 1C, the plunger 152 is held stationary against the plunger guard 110, and as fluid is removed (e.g., pumped) from the large syringe 150 (reducing fluid pressure within the barrel 156), the barrel 156 moves down towards the plunger 152 by way of gravity. Because the syringe clamp 130 is securely attached to the barrel 156, the syringe clamp 130 also moves down as the barrel 156 moves down. In some implementations, the syringe clamp 130 is weighted to provide additional gravitational assist to the fluid delivery system 200. Additionally, the weight of the barrel 156 and fluid within may push the flange 154 down, may assist in pushing against the syringe flange slot 136 to also assist in pushing down the syringe clamp 130. The syringe clamp 130 may freely slide along the support bar 120 so as not to impede the movement of the barrel 156 from gravity. The syringe clamp 130 remains slidably connected to the support bar 120 to prevent the large syringe 150 from tipping over or otherwise falling out of the syringe holder 100.

In certain implementation, the downward movement of the syringe clamp 130 may be augmented or assisted by a syringe assist mechanism. For instance, the stiction forces of smaller syringes (such as the small syringe 160 and/or the micro syringe 170) may make the accurate and consistent delivery of medication to a patient more difficult for the fluid delivery system 200. The syringe clamp 130 may be aided with extra weight such as 30 g, or with a rack pinion-and-gear with a spring mechanism to assist the barrel 154 to move down towards the plunger 172.

Figure 2A:
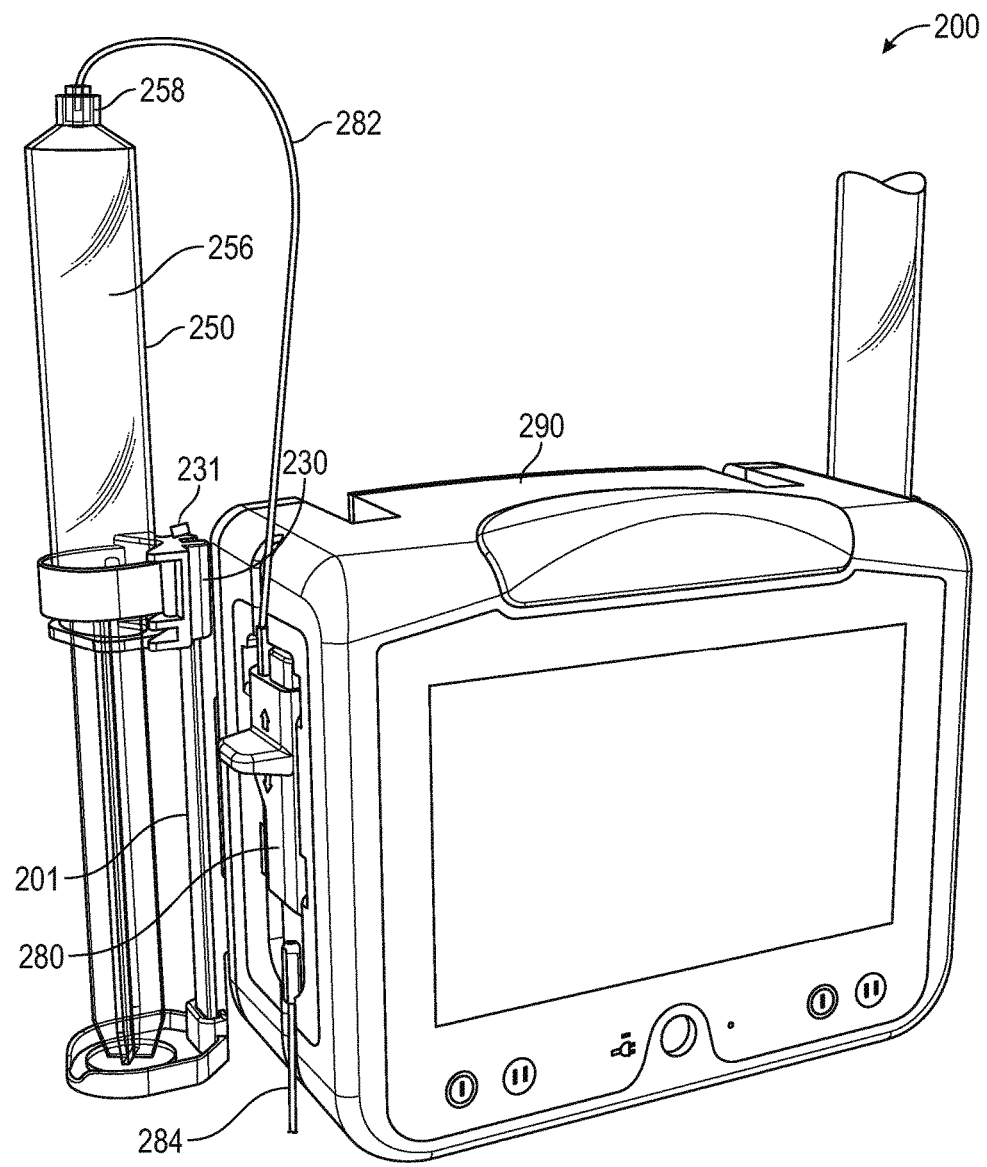
FIG. 2A illustrates a perspective view of a fluid delivery system having a syringe holder, in accordance with aspects of the present disclosure.
Figure 2B:
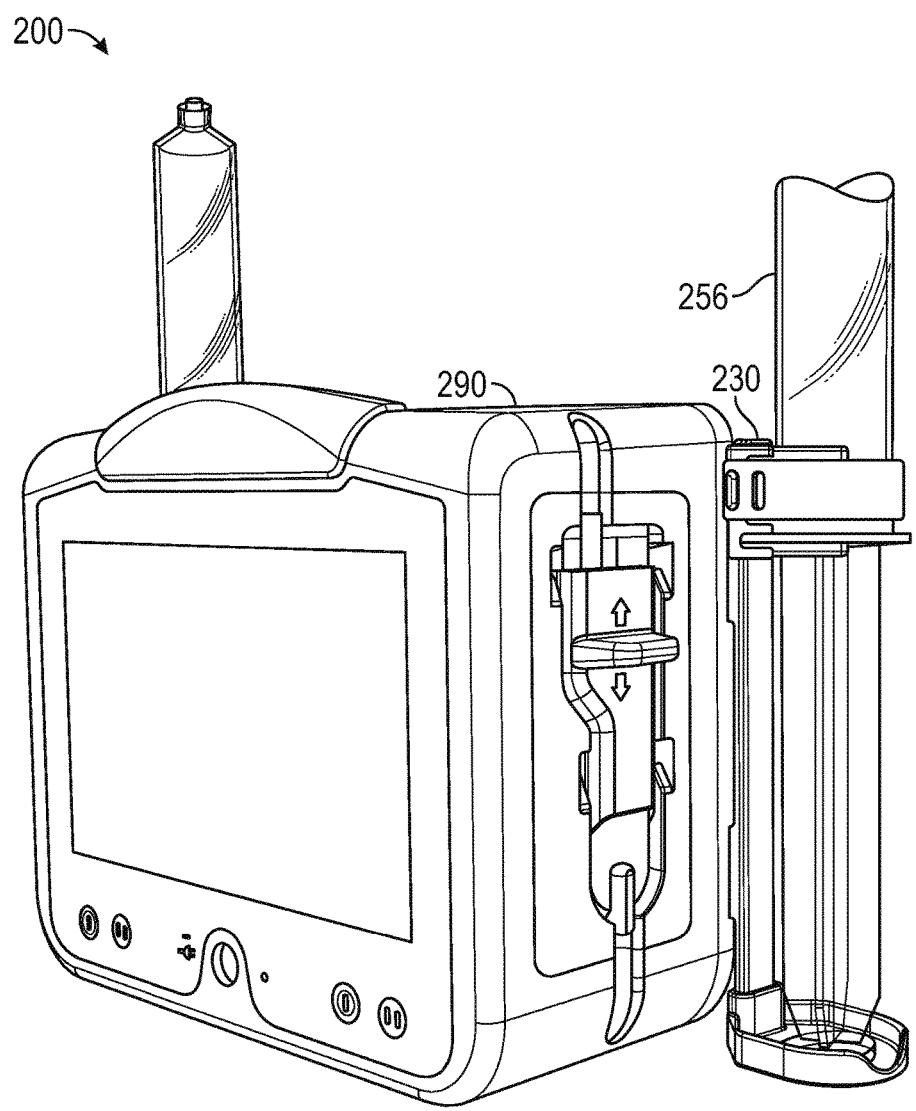
FIG. 2B illustrates another perspective view of the fluid delivery system of FIG. 2A, showing the syringe holder in a home position, in accordance with aspects of the present disclosure.
Figure 2C:
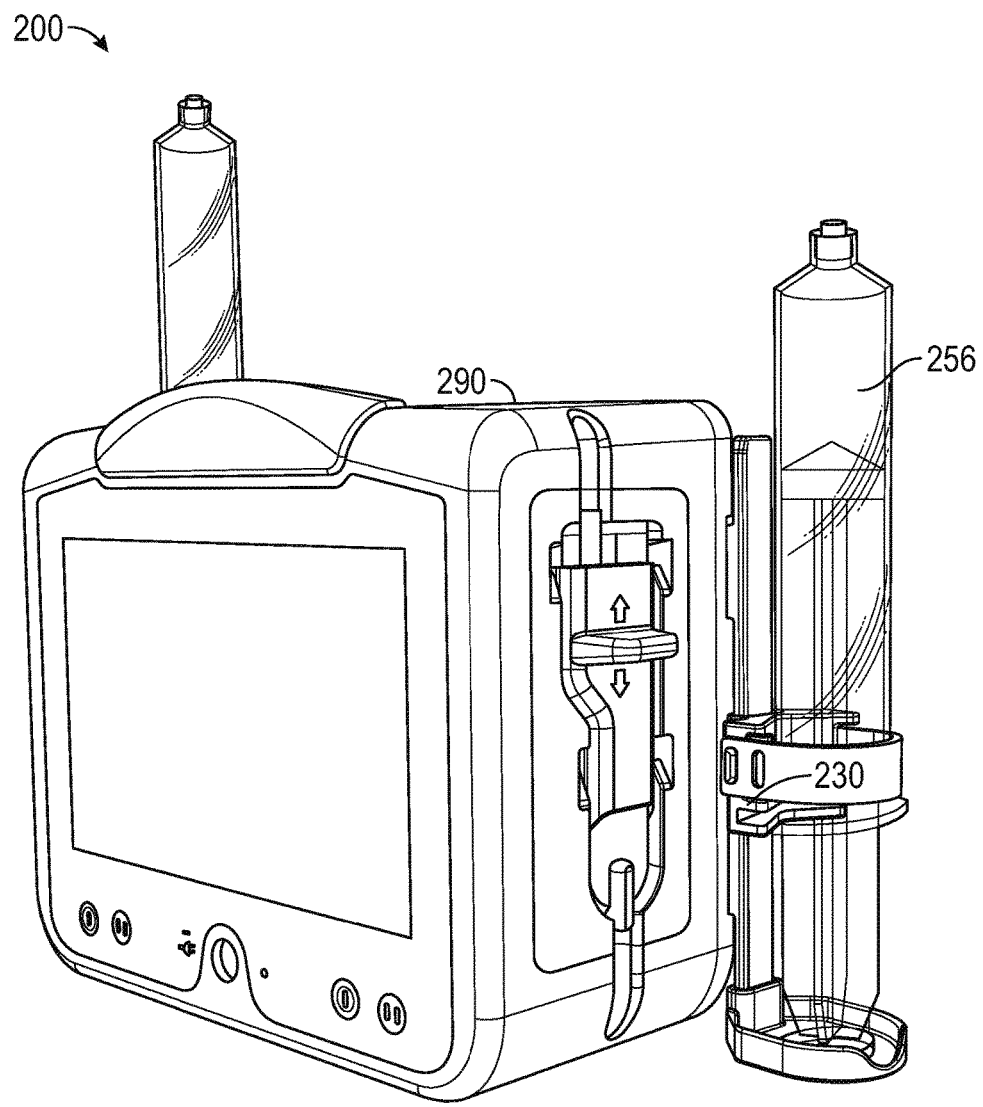
FIG. 2C illustrates the fluid delivery system of FIG. 2B, having the syringe holder shifted from the home position, in accordance with aspects of the present disclosure.

FIGS. 2A-2C depict a fluid delivery system 200, which may be an infusion device. The fluid delivery system 200 comprises a main body 290, an IV cassette 280, a fluid line 282, a fluid output line 284, and a syringe holder 201. The syringe holder 201 comprises a syringe clamp 230. The syringe holder 201 holds a large syringe 250 comprising a barrel 256 and tip 258.

The fluid line 282 (not shown in FIGS. 2B and 2C) creates a fluid path from the large syringe 250 to the IV cassette 280. The IV cassette 280 may include a pump for pumping fluid from the tip 258 of the large syringe 250. As seen in FIG. 2A, the fluid in the large syringe 250 is extracted out or of the large syringe 250 and the fluid is pumped through the fluid output line 284 (not shown in FIGS. 2B and 2C) for connecting to, for example, other downstream components or a patient.

The syringe holder 201 corresponds to the syringe holder 100. The syringe clamp 230 is securely attached to the barrel 256. As seen in FIGS. 2B and 2C, the syringe clamp 230 moves down along with the barrel 256 as fluid within the large syringe 250 is pumped out.

Figure 3:
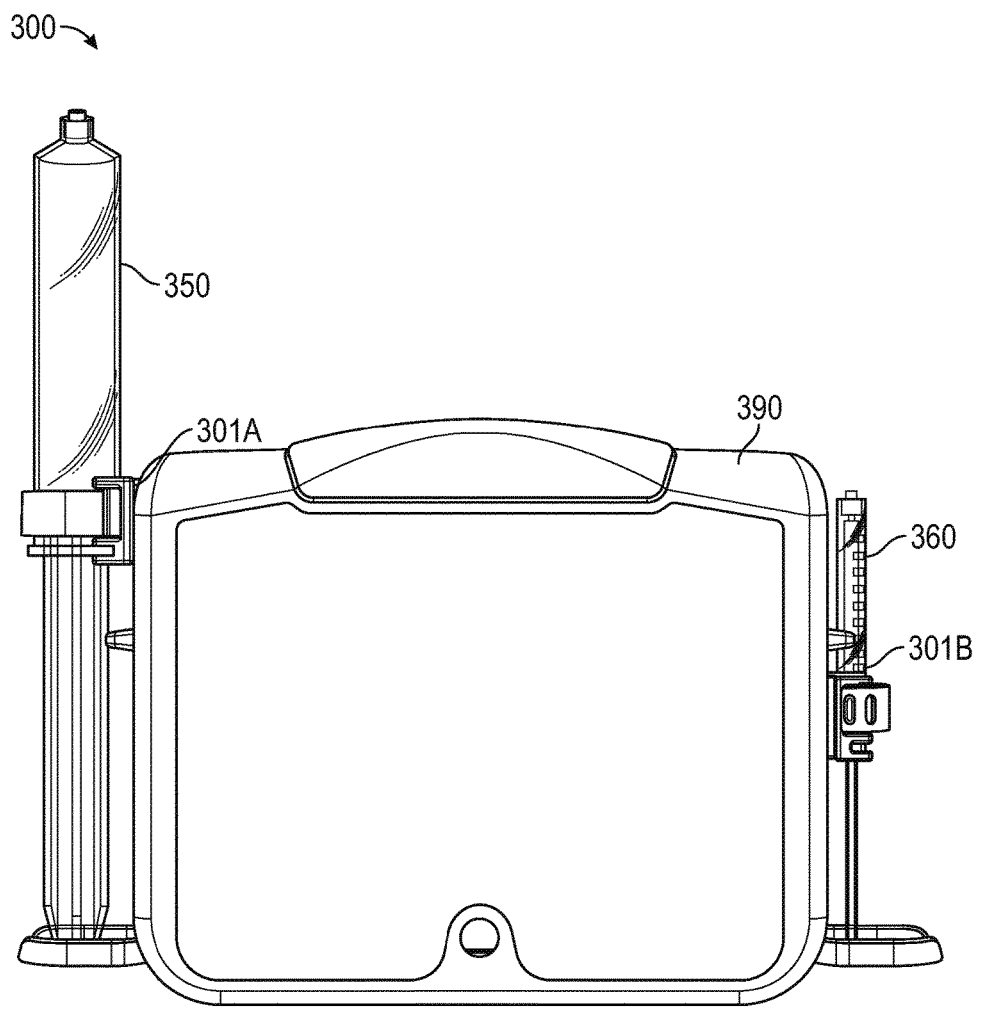
FIG. 3 illustrates a front view of an example of a fluid delivery system, in accordance with aspects of the present disclosure.

FIG. 3 shows a fluid delivery system 300, which may be an infusion device. The fluid delivery system 300 comprises a main body 390, a first syringe holder 301A, and a second syringe holder 301B. FIG. 3 shows that the syringe holders can hold different size syringes. The first syringe holder 301A holds a large syringe 350 and the syringe holder 301B holds a small syringe 360.

Figure 4:
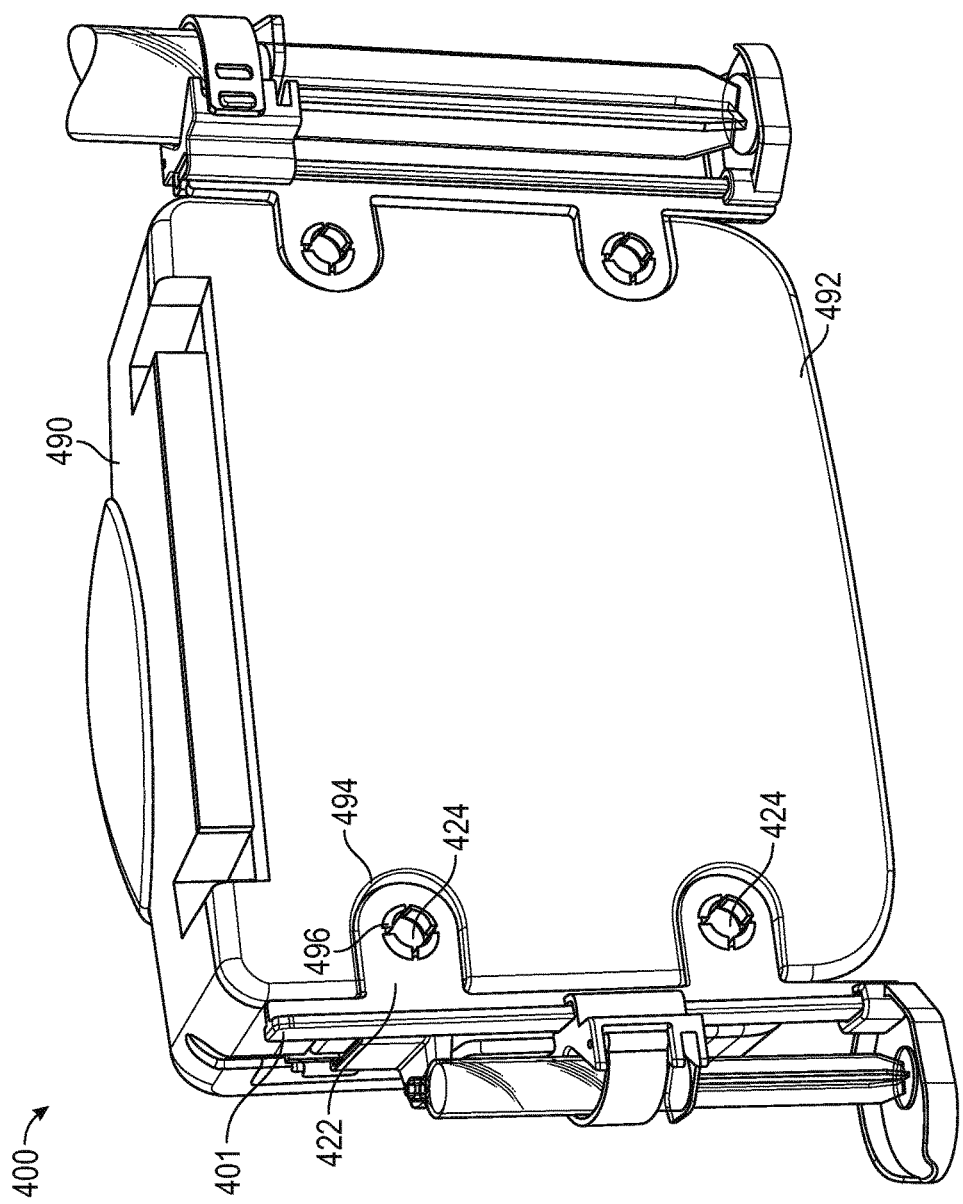
FIG. 4 illustrates a back-side view of an example of a fluid delivery system, in accordance with aspects of the present disclosure.

FIG. 4 depicts a fluid delivery system 400, which may be an infusion device. The fluid delivery system 400 comprises a main body 490 having a back side 492, and a syringe holder 401. The syringe holder 401 comprises a support tab 422 which defines a hole 424. The back side 492 includes an indent 494 and an extension 496. The support tab 422 fits into the indent 494 and the extension 496 fits through the hole 424 in order to support and hold the syringe holder 401 to the main body 490. In other implementations, the syringe holder 401 may be attached to other walls of the main body 490 rather than the back side 492.

Figure 5A:
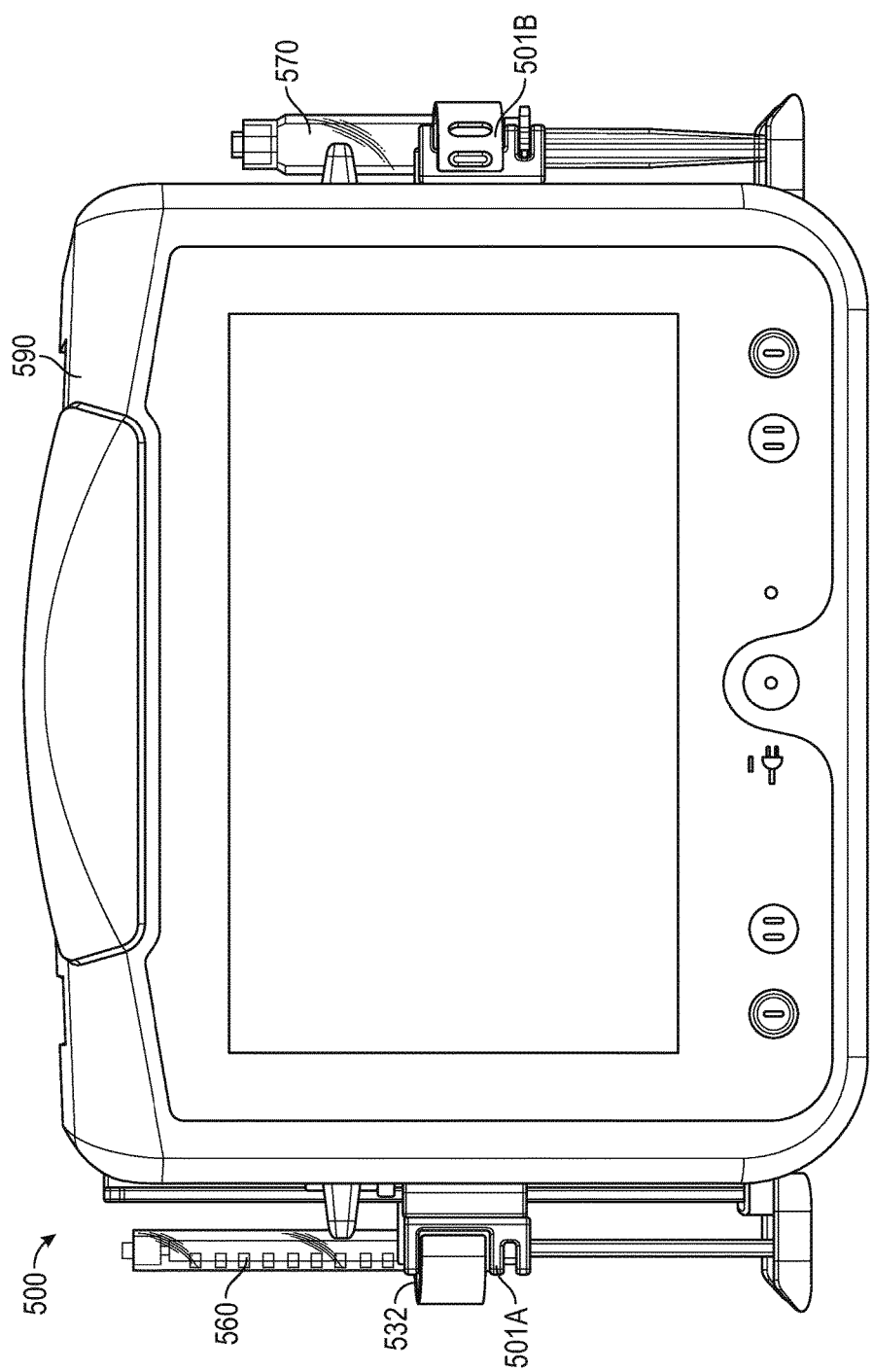
FIG. 5A illustrates a front view of an example of a fluid delivery system, in accordance with aspects of the present disclosure.
Figure 5B:
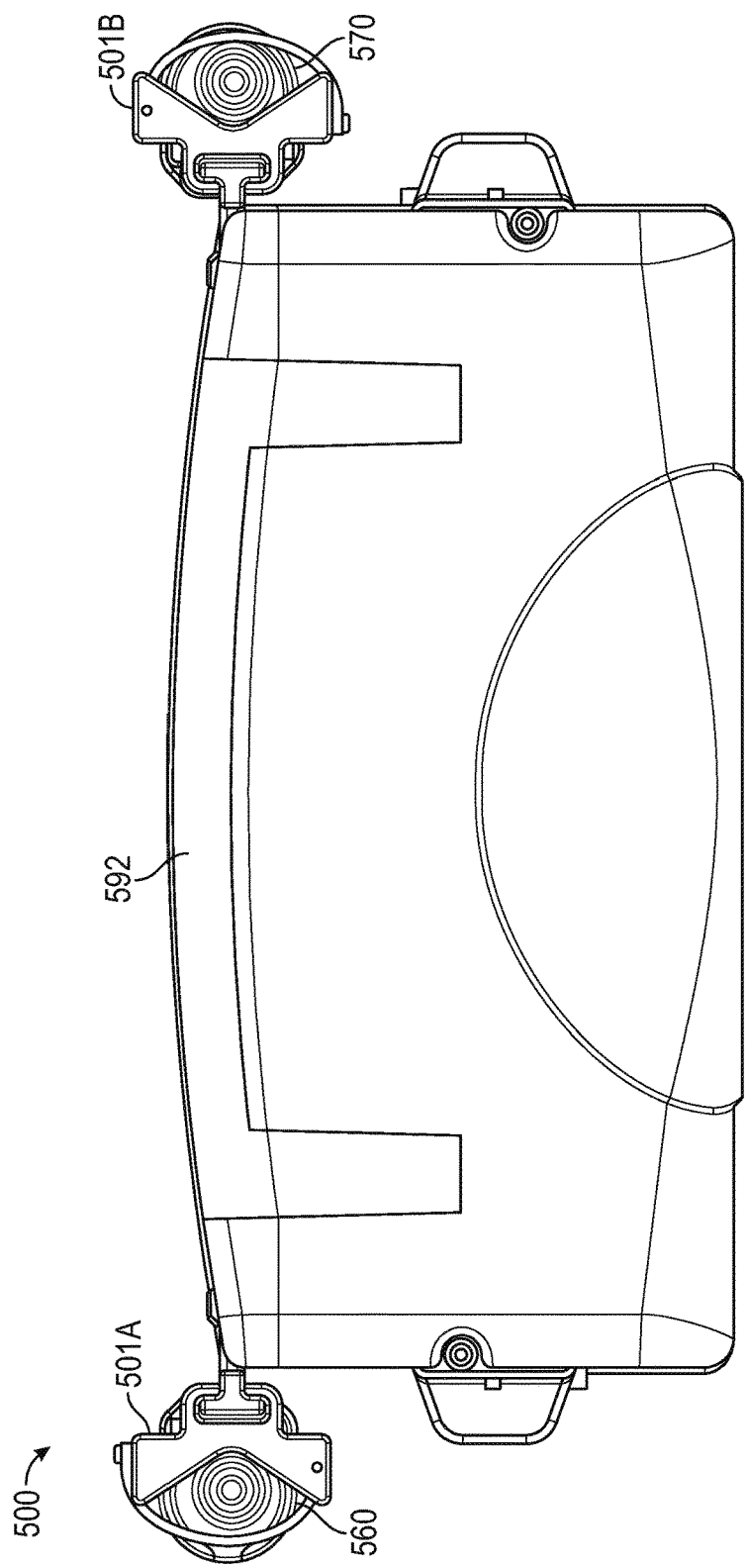
FIG. 5B illustrates a top-down view of the example fluid delivery system of FIG. 5A, in accordance with aspects of the present disclosure.
Figure 5C:
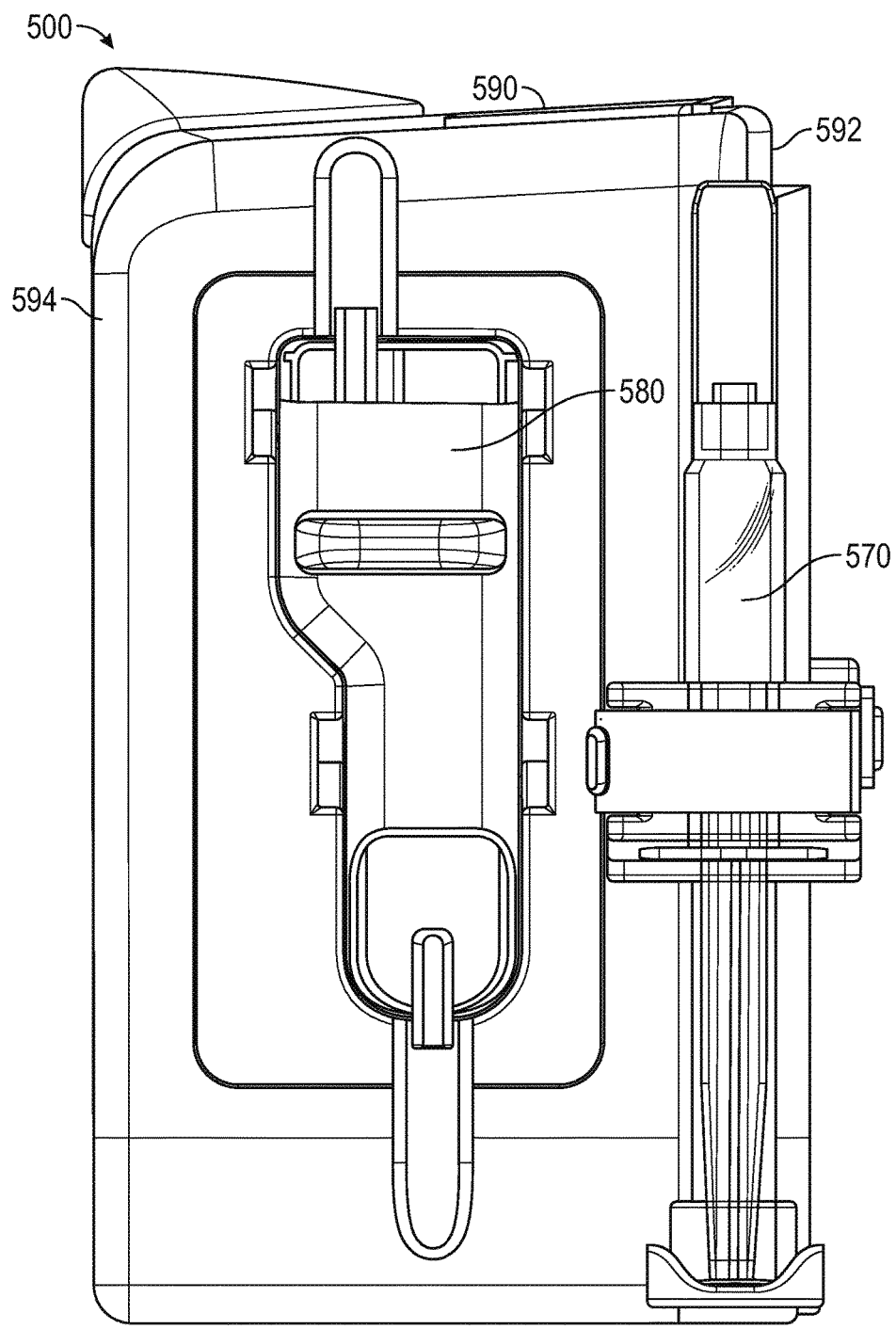
FIG. 5C illustrates a side view of the example fluid delivery system of FIG. 5A, in accordance with aspects of the present disclosure.

FIGS. 5A-5C depict a fluid delivery system 500, which may be an infusion device. The fluid delivery system 500 includes a main body 590 having a side wall 594 (FIG. 5C), a back side 592 (in FIGS. 5B and 5C), an IV cassette 580 (in FIG. 5c), a first syringe holder 501A, and a second syringe holder 501B. The first syringe holder 501A includes a hinged band 532 for holding a small syringe 560. The second syringe holder 501B holds a micro syringe 570. FIGS. 5A-5C illustrate another combination of syringe sizes. Because the first and second syringe holders 501A and 501B are configured to hold various syringe sizes, any two sizes of syringes can be used. The top-down view in FIG. 5B illustrate how the first and second syringe holders 501A and 501B extend laterally from the back side 592.

FIG. 5C shows a side view of the fluid delivery system 500. As seen in FIG. 5C, the lateral placement of the syringe holders allows for unobstructed access to the syringe (micro syringe 570 in FIG. 5C), as well as the IV cassette 580, which is embedded in the side wall 594. However, in other implementation, other arrangements may be used. For instance, the syringe holders may be attached to the side wall 594 such that the syringe holders extend away from the back side 592. The syringe holders may be attached to other portions of the main body 590 while maintaining a vertical orientation.

Figure 6A:
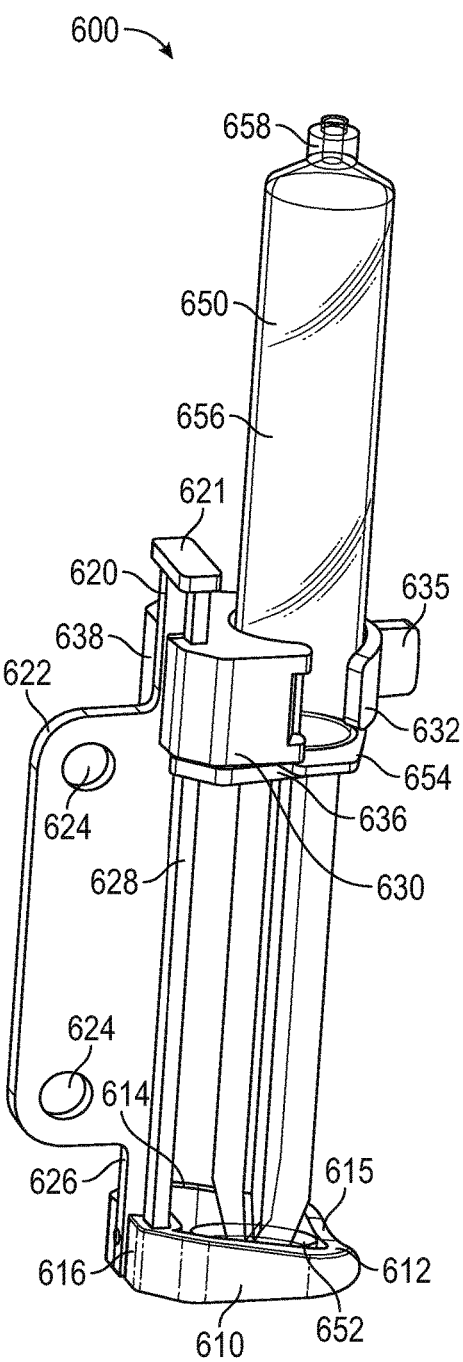
FIG. 6A illustrates a side view of a second example syringe holder holding a large syringe, in accordance with aspects of the present disclosure.
Figure 6B:
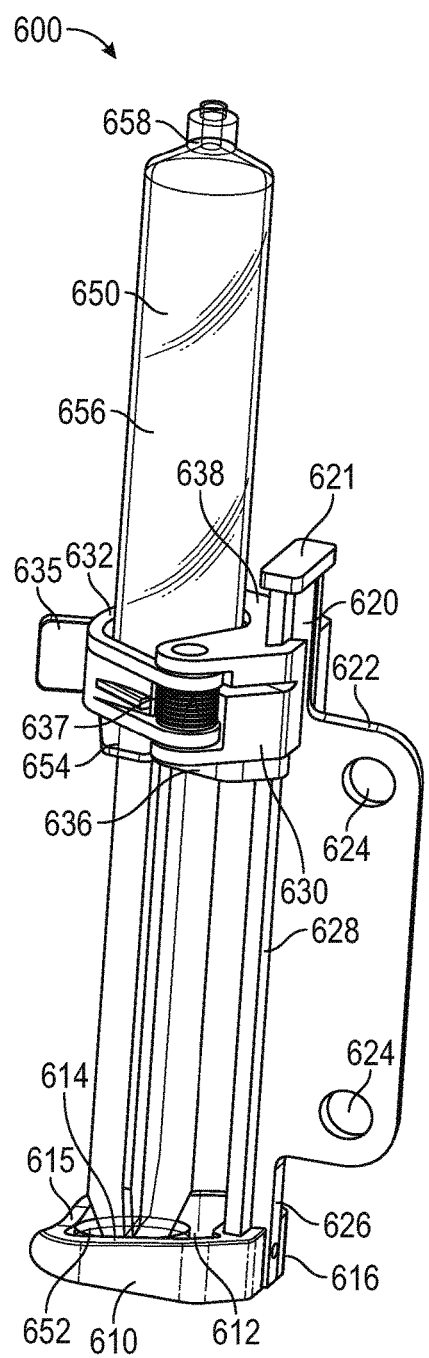
FIG. 6B illustrates an alternate side view of the syringe holder of FIG. 6A.

FIGS. 6A-6B illustrate another implementation of a syringe holder 600. FIGS. 6A and 6B generally show alternative side views of the syringe holder 600. The syringe holder 600 comprises a plunger guard 610, support bar 620, and syringe clamp 630. The plunger guard 610 comprises a seating surface 612, a guard wall 614, a gap 615, and a base connector 616. The support bar 620 comprises a stopper 621, a support tab 622, a spine 626, and a support surface 628. The support tab 622 defines two holes 624. The syringe clamp 630 comprises a band 632, a tab 635, a syringe flange slot 636, a spring mechanism 637, and a sliding portion 638.

The syringe holder 600 is configured to hold syringes of various sizes without interfering with other devices in the system. For example, in FIGS. 6A and 6B, the syringe holder 600 holds a large syringe 650. The large syringe 650, which may correspond to the large syringe 150, comprises a plunger 652, a flange 654, a barrel 656, and a tip 658. The syringe size is not limiting and may vary within the scope of the present disclosure.

The plunger guard 610 may be a single piece or may comprise several connected pieces. The plunger guard 610 is made of a hard material, such as plastic, but in other implementations may be made of other rigid or resilient materials. The plunger guard 610 is configured, similar to the plunger guard 110 in FIG. 1, to provide a stable surface, such as the seating surface 612, to hold a syringe. As seen in FIGS. 6A and 6B, the seating surface 612 holds the plunger 652 stationary.

The seating surface 612 may be made of a non-slip material to further prevent the plunger 652 from shifting. The guard wall 614 is configured to prevent the plunger 652 from shifting out of the seating surface 612. The guard wall 614 partially encircles the syringe 650. The gap 615 in the guard wall 614 may allow for easier insertion and extraction of the plunger 652 from the plunger guard 610. In certain implementations, the guard wall 614 may extend higher, for example beyond a midpoint of the support bar 620, to provide greater protection to the syringe 659 (e.g., from bumps), and to further prevent the syringe 650 from falling out or other accidental removal.

The base connector 616 of the plunger guard 610 is configured to connect to the support bar 620. The base connector 616 may be shaped complementary to the support bar 620 such that the base connector 616 mates with the support bar 620 to provide a stable connection that does not allow the support bar 620 to move, and the base connector 616 to be removed from the support bar 620. The support bar 620 is vertically oriented such that it generally extends along an axis parallel to a syringe axis, which extends from the tip 658 to the plunger 652 of the syringe 650 when the syringe 650 is held in the syringe holder 600.

The support bar 620 is made of a hard material, such as plastic, or alternatively be made of another hard material. The support bar 620 comprises a single molded piece, but in other implementations may comprise several multiple connected pieces. The support bar 620 is a separate piece from the plunger guard 610 but in other implementations may be integrated with, co-molded with, or otherwise forms a single piece with the plunger guard 610. The support bar 620 comprises the spine 626 meeting the support surface 628 in a T-bar. In other implementations, the support bar 620 may comprise any other structure capable of remaining rigid. The support bar 620 comprises the stopper 621 at a top of the support bar 620, which may prevent the syringe clamp 630 from sliding off the support bar 620. The spine 626 further comprises the support tab 622, which defines the holes 624. The support tab 622 and the holes 624 are configured to connect the syringe holder 600 to another device, such as a fluid delivery device. Although the support bar 620 comprises the support tab 622 and the holes 624 for attachment, in other implementations other attachment mechanisms may be used. For example, the support tab 622 may comprise protrusions for snapping into a fluid delivery device, or may use magnets for attachment. In addition, the support tab 622 extends generally perpendicular to the syringe holder 600. However, in other implementations the support tab 622 may extend at other angles.

The support surface 628 further forms a set of rails, as the support surface 628 extends laterally from the spine 626. The sliding portion 638 of the syringe clamp 630 is configured to wrap around or mate with the support surface 628 such that the syringe clamp 630 can slide up and down the support bar 620. When the syringe clamp 630 is in a home position, in which the syringe clamp 630 is at the stopper 621, the syringe clamp 630 may be configured to lock into the home position to prevent sliding. The syringe clamp 630 may be locked into the home position through mechanical means such as magnets, springs, or a protrusion fitting into a groove. When no syringe is inserted, the syringe clamp 630 may remain in the home position for easier syringe loading. In certain implementations, a sensor, such as a Hall effect sensor, may detect when the syringe clamp 630 is locked in the home position. In certain implementations, the sensor may further detect when a syringe is loaded and the syringe clamp 630 is locked in the home position, and may signal a warning to alert a user that the syringe clamp 630 is locked in the home position.

The syringe clamp 630 comprises a radial clamp comprising the band 632 and the spring mechanism 637. The band 632 is made of a hard or rigid material such as plastic and comprises the tab 635. The band 632 pivots around one end of the syringe clamp 630, having the spring mechanism 637. The spring mechanism 637 comprises a spring configured to hold the band 632 closed against the sliding portion 638. As seen in FIGS. 6A and 6B, the band 632 closes around the syringe 650. In other implementations, the spring mechanism 637 may comprise a resilient material or other resistive element. The tab 635 allows pushing the band 632 against the force of the spring mechanism 637 to open the band 632. The band 632 is configured to close around syringes of various sizes.

The syringe clamp 630 also comprises a syringe flange holder 636 configured to receive the syringe flange 654. The syringe flange holder 636, in conjunction with the band 632, securely attaches the syringe clamp 630 to the syringe 650. More specifically, the syringe clamp 630 securely attaches with the barrel 656 and is configured to move along with the barrel 656, similar to the movement of the syringe claim 130 described herein.

FIGS. 7A-7B illustrate another implementation of a syringe holder 700. FIGS. 7A and 7B show alternate side views of the syringe holder 700. The syringe holder 700 comprises a stationary plunger guard 710, support bar 720, and syringe clamp 730. The plunger guard 710 comprises a seating surface 712, a guard wall 714, a gap 715, and a base connector 716. The support bar 720 comprises a stopper 721, a support tab 722, a spine 726, and a support surface 728. The support tab 722 defines holes 724. Screws 725 are disposed within the holes 724. The syringe clamp 730 comprises a band 732 and a sliding portion 738. The band 132 comprises a lip 739 and defines a first chamber 731 and a second chamber 733.

The syringe holder 700 is configured to hold two syringes without interfering with other devices in the system. For example, in FIGS. 7A and 7B, the syringe holder 700 holds a large syringe 750 in the second chamber 733 and a small syringe 770 in the first chamber 731. The large syringe 750 comprises a plunger 752, a flange 754, a barrel 756, and a tip 758. The small syringe 770 comprises a plunger 772, a flange 774, a barrel 776, and a tip 778.

The large syringe 750 may correspond to the large syringe 150. The small syringe 770 may correspond to the small syringe 160 or the micro syringe 170. The syringe sizes are not limiting and may vary within the scope of the present disclosure. However, the large syringe 750 corresponds to a syringe larger than the small syringe 770.

The plunger guard 710 may be a single piece or may comprise several connected pieces. The plunger guard 710 is made of a hard material, such as plastic, but in other implementations may be made of other rigid or resilient materials. The plunger guard 710 is configured, similar to the plunger guard 110, to provide a stable surface, such as the seating surface 712, to hold one or more syringes. The plunger guard 710 may be larger than the plunger guard 110 and is configured to hold multiple syringes, such as the large syringe 750 and the small syringe 770.

The seating surface 712 may be made of a non-slip material to further prevent plungers from shifting. The guard wall 714 is configured to prevent the plungers from shifting out of the seating surface 712. The guard wall 714 partially encircles the syringes. The gap 715 in the guard wall 714 may allow for easier insertion and extraction of the plungers from the plunger guard 710. In certain implementations, the guard wall 714 may extend higher, for example beyond a midpoint of the support bar 720, to provide greater protection to the syringes (e.g., from bumps), and to further prevent the syringes from falling out or other accidental removal.

The base connector 716 of the plunger guard 710 is configured to connect to the support bar 720. The base connector 716 may be shaped complementary to the support bar 720 such that the base connector 716 mates with the support bar 720 to provide a stable connection that does not allow the support bar 720 to move, and the base connector 716 to be removed from the support bar 720. The support bar 720 is vertically oriented such that it generally extends along an axis parallel to a syringe axis, which extends from a tip to a plunger of a syringe when the syringe is held in the syringe holder 700.

The support bar 720 is made of a hard material, such as plastic, or alternatively be made of another hard material.

The support bar 720 comprises a single molded piece, but in other implementations may comprise several multiple connected pieces. The support bar 720 is a separate piece from the plunger guard 710 but in other implementations may be integrated with, co-molded with, or otherwise forms a single piece with the plunger guard 710. The support bar 720 comprises the spine 726 meeting the support surface 728 in a T-bar. In other implementations, the support bar 720 may comprise any other structure capable of remaining rigid. The support bar 720 comprises the stopper 721 at a top of the support bar 720, which may prevent the syringe clamp 730 from sliding off the support bar 720. The spine 726 further comprises the support tab 722, which defines the holes 724 for holding the screws 725. The support tab 722, the holes 724, and the screws 725 are configured to connect the syringe holder 700 to another device, such as a fluid delivery device. Although the support bar 720 comprises the support tab 722 and the holes 724 for attachment through the screws 725, in other implementations other attachment mechanisms may be used. For example, the support tab 722 may comprise protrusions for snapping into a fluid delivery device, or may use magnets for attachment. In addition, the support tab 722 extends generally perpendicular to the syringe holder 700. However, in other implementations the support tab 722 may extend at other angles.

The support surface 728 further forms a set of rails, as the support surface 728 extends laterally from the spine 726. The sliding portion 738 of the syringe clamp 730 is configured to wrap around or mate with the support surface 728 such that the syringe clamp 730 can slide up and down the support bar 720. When the syringe clamp 730 is in a home position, in which the syringe clamp 730 is at the stopper 721, the syringe clamp 730 may be configured to lock into the home position to prevent sliding. The syringe clamp 730 may be locked into the home position through mechanical means such as magnets, springs, or a protrusion fitting into a groove. When no syringe is inserted, the syringe clamp 730 may remain in the home position for easier syringe loading. In certain implementations, a sensor, such as a Hall effect sensor, may detect when the syringe clamp 730 is locked in the home position. In certain implementations, the sensor may further detect when a syringe is loaded and the syringe clamp 730 is locked in the home position, and may signal a warning to alert a user that the syringe clamp 730 is locked in the home position.

The syringe clamp 730 comprises the band 732. The band 732 is made of a hard or rigid material such as plastic and comprises the lip 739. The band 732 defines the first chamber 731 and the second chamber 733. The first chamber 731 is configured to hold the small syringe 770 such that a radius of the first chamber 731 corresponds to a radius of the small syringe 770. The second chamber 733 is configured to hold the large syringe 750 such that a radius of the second chamber 733 corresponds to a radius of the large syringe 750. The lip 739 extends outwards such that the band 732 is not closed. The opening in the band 732 allows for some flexibility to insert syringes into the first chamber 731 and/or the second chamber 733. The syringes may be inserted laterally through the opening and past the lip 739, which extends outwards to provide a smooth surface without sharp corners. Alternatively, the syringes may be inserted vertically into the respective first chamber 731 and/or the second chamber 733.

A syringe is vertically oriented upside down in the syringe holder 100. For example in FIG. 1C, the plunger 152 is upside down such that the plunger 152 is at the bottom and the tip 158 is at the top. Fluid within the large syringe 150 is extracted through the tip 158, against gravity. Similarly, the small syringe 160 is vertically oriented upside down in FIG. 1D, and the micro syringe 170 is vertically oriented upside down in FIGS. 1E and 1F. In FIG. 1C, the plunger 152 is held stationary against the plunger guard 110, and as fluid is removed (e.g., pumped) from the large syringe 150 (reducing fluid pressure within the barrel 156), the barrel 156 moves down towards the plunger 152 by way of gravity. Because the syringe clamp 130 is securely attached to the barrel 156, the syringe clamp 130 also moves down as the barrel 156 moves down. In some implementations, the syringe clamp 130 is weighted to provide additional gravitational assist to the fluid delivery system 200. Additionally, the weight of the barrel 156 and fluid within may push the flange 154 down, may assist in pushing against the syringe flange slot 136 to also assist in pushing down the syringe clamp 130. The syringe clamp 130 may freely slide along the support bar 120 so as not to impede the movement of the barrel 156 from gravity. The syringe clamp 130 remains slidably connected to the support bar 120 to prevent the large syringe 150 from tipping over or otherwise falling out of the syringe holder 100.

Figure 8:
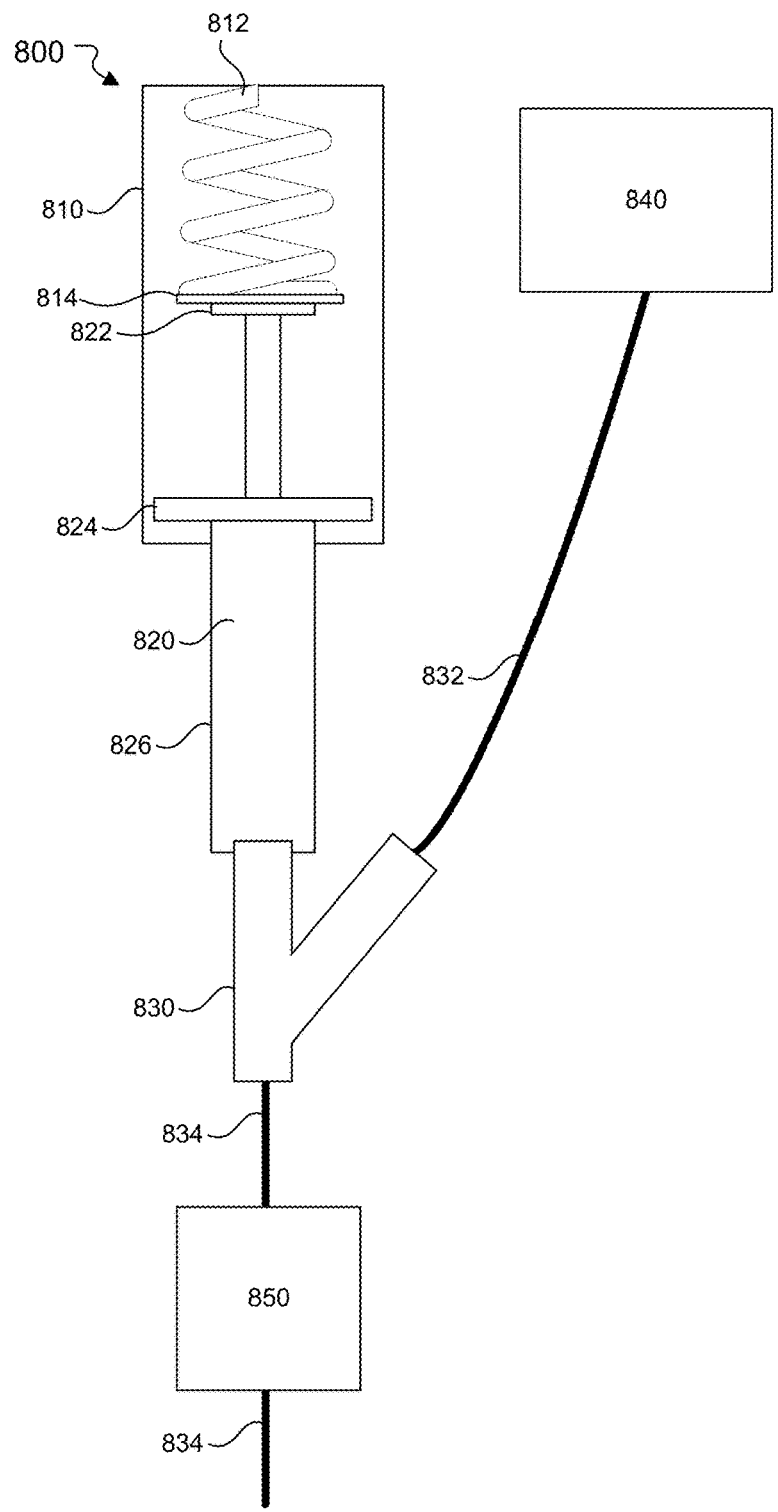
FIG. 8 shows a diagram view of a syringe adapter, in accordance with aspects of the present disclosure.

FIG. 8 shows a diagram of an alternative implementation of the present invention including a syringe holder or adapter 800. The syringe adapter 800 includes a housing 810, a follower 814, and a spring mechanism or spring 812. The follower 814 and the spring 812 may be disposed within the housing 810. The syringe adapter 800 is mounted on a syringe 820, which includes a plunger 822, a flange 824, and a barrel 826. The housing 810 is configured to enclose at least the plunger 822 and may also enclose the flange 824 and a portion of the barrel 826. The syringe 820 is connected to a Y-site 830. The Y-site 830 is connected through a fluid line 832 to a primary bag 840, and is also connected through a fluid line 834 to a pump 850. Optionally, a check valve may be connected between the primary bag 840 and the Y-site 830.

The spring 812 is configured to apply a continuous force or load on the plunger 822 through contact with the follower 814, creating a positive pressure. The positive pressure prevents air from being drawn in, and also maintains a consistent flow to the pump 850. The positive pressure can also ensure that a check valve remains closed until the syringe 820 infusion is complete. The syringe adapter 800 can be used on any size syringe, and also allows syringe infusion at any altitude because the syringe adapter 800 can compensate for reduced atmospheric pressure. The syringe adapter 800 can stay attached to the syringe 820 so that the operator can observe the amount of fluid left in the syringe 820. The syringe adapter 800 is placed upstream from the pump 850, which controls the infusion parameters.

The syringe adapter 800 attaches to the flange 824, and the follower 814 and the spring 812 are free to apply force against the plunger 822. In certain implementations, a feature causes the follower 814 to retract against the spring 812 as the housing 810 is opened. For example, the feature may be a lever which prevents the follower 814 from moving when the housing 810 is opened. When the housing 810 is closed, the feature allows the follower 814 to engage the plunger 822. For example, the feature may be a lever which is released when the housing 810 is closed, allowing the follower 814 to move. In certain implementations, the follower 814 is retracted until the housing 810 is closed, which allows the follower 814 to engage the plunger 822. The follower 814 would not be able to be re-cocked such that the syringe adapter 800 could not be reused.

Figure 9:
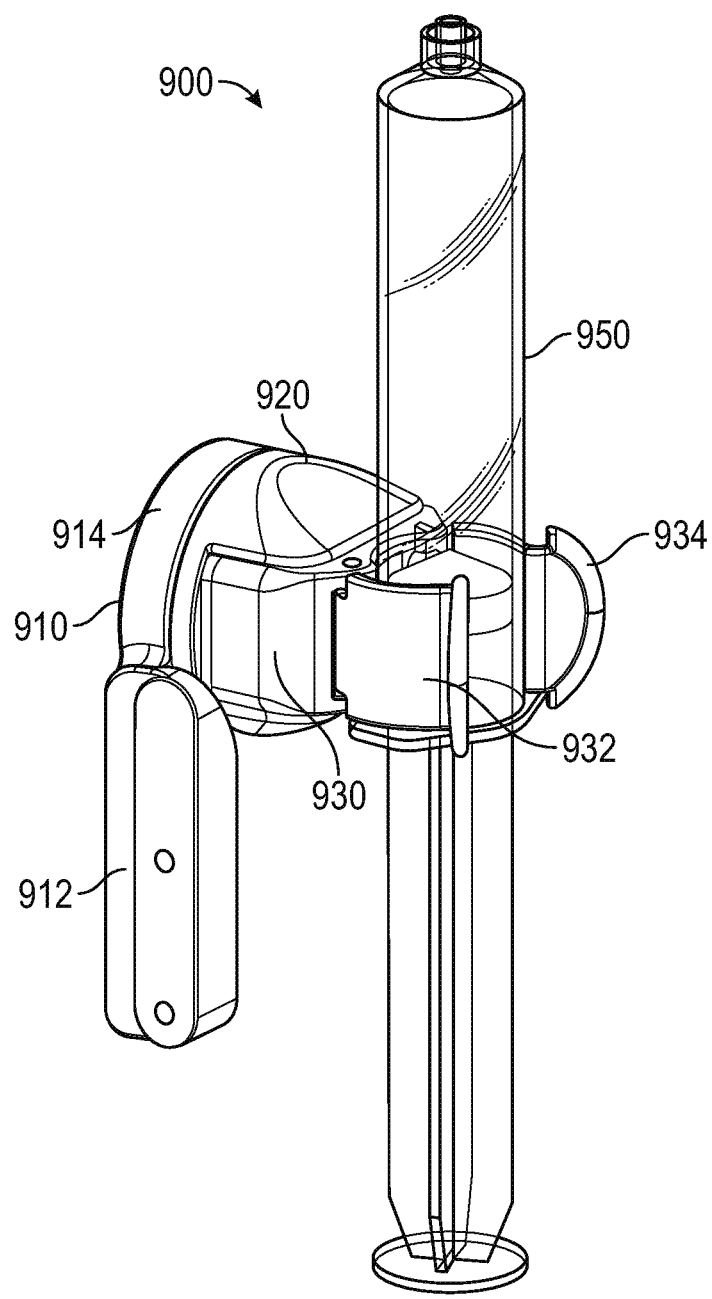
FIG. 9 illustrates a rotating syringe holder, in accordance with aspects of the present disclosure.

FIGS. 9-13E illustrate further implementations of a syringe holder 900. In FIG. 9, the syringe holder 900 comprises a base 910, a swivel 920, and a syringe clamp 930. The base 910 comprises an attachment portion 912 and a pivot portion 914. The syringe clamp 930 comprises a syringe clamp arm 932 having an outward projection 934. In FIG. 9, the syringe clamp 930 is configured to hold a syringe 950 and includes a pair of syringe clamp arms 932 forming a C-clamp, although in other implementations the syringe claim 930 may hold the syringe 950 through other mechanical means, such as a band or radial clamp as described herein. The swivel 920 couples the pivot portion 914 of the base 910 to the syringe clamp 930, providing relative rotational movement between the base 910 and the syringe clamp 930.

FIGS. 10A-10F show a syringe holder 1000 that may correspond to the syringe holder 900. FIGS. 10A-10D illustrate rotation of the swivel. The syringe holder 1000 comprises a base 1010, a swivel 1020, and a syringe clamp 1030. The base 1010 comprises an attachment portion 1012 and a pivot portion 1014. The syringe clamp 1030 comprises a syringe clamp arm 1032 having an outward projection 1034, and a pad 1036 that is configured to prevent the syringe from sliding as well as provide cushion against the syringe clamp 1030 and may be made of a non-slip material. The swivel 1020 couples the pivot portion 1014 of the base 1010 to the syringe clamp 1030, providing relative rotational movement between the base 1010 and the syringe clamp 1030 about a pivot axis 1001. In FIGS. 10A-10D, the syringe clamp 1030 is in an open position, having the syringe clamp arms 1032 apart, to show the syringe clamp 1030. However, the syringe clamp 1030 may normally be in a closed position, with the syringe clamp arms 1032 together, when the syringe clamp 1030 is not holding the syringe.

FIGS. 10A-10D illustrate the pivot axis 1001. The pivot axis 1001 is defined by the swivel 1020, such that the swivel 1020 pivots or rotates about the pivot axis 1001. In FIGS. 10A-10D, the pivot axis 1001 corresponds to a center of a circle defined by the shape of the swivel 1020, although in other implementations the pivot axis 1001 may be located elsewhere with respect to the swivel 1020, which is not limited to a circular shape. The swivel 1020 comprises a first portion 1022 and a second portion 1024 defining a cavity between the first portion 1022 and the second portion 1024 for receiving the syringe clamp 1030. The syringe clamp 1030 is configured to move with the swivel 1020 as the swivel 1020 rotates. The syringe clamp 1030 may be configured to not move with respect to the swivel 1020, although in other implementations, the syringe clamp 1030 may move side-to-side or pivot with respect to the swivel 1020 for additional articulation.

An orientation of the syringe clamp 1030 may be defined with respect to a zero degree heading 1003 and a current heading 1004. The zero degree heading 1003 may, as seen in FIG. 10C, indicate the syringe clamp 1030 at 0 degrees, corresponding to an orientation which holds a syringe vertically. For the syringe clamp 1030 having the syringe clamp arms 1032 in a C-clamp configuration, the zero degree heading 1003 corresponds to the sides, at 90 degrees and 180 degrees. The zero degree heading 1003 and the current heading 1004 provide reference points for describing the orientation of the syringe clamp 1030 but any reference point system may be used to determine the orientation the syringe clamp 1030 without limiting aspects of the present disclosure. The angle formed between the zero degree heading 1003 and the current heading 1004 determines the current angle of the syringe clamp 1030. The angle may be described as positive (clockwise from the zero degree heading 1003) or negative (counter-clockwise from the zero degree heading 1003).

In FIG. 10C, the current heading 1004 is 90 degrees, which corresponds to 90 degrees clockwise from the zero degree heading 1003 in FIG. 10C. At 90 degrees, the syringe clamp 1030 holds the syringe horizontally. The swivel 1020 may be configured to rotate freely, from 0-360 degrees or 0 to −360 degrees, or may be configured to rotate between a first angle and a second angle, such as between −90 and 90 degrees. The swivel 1020 may be configured with a detent mechanism to lock at certain angles, as will be further described herein.

Figures 10A, 10B:
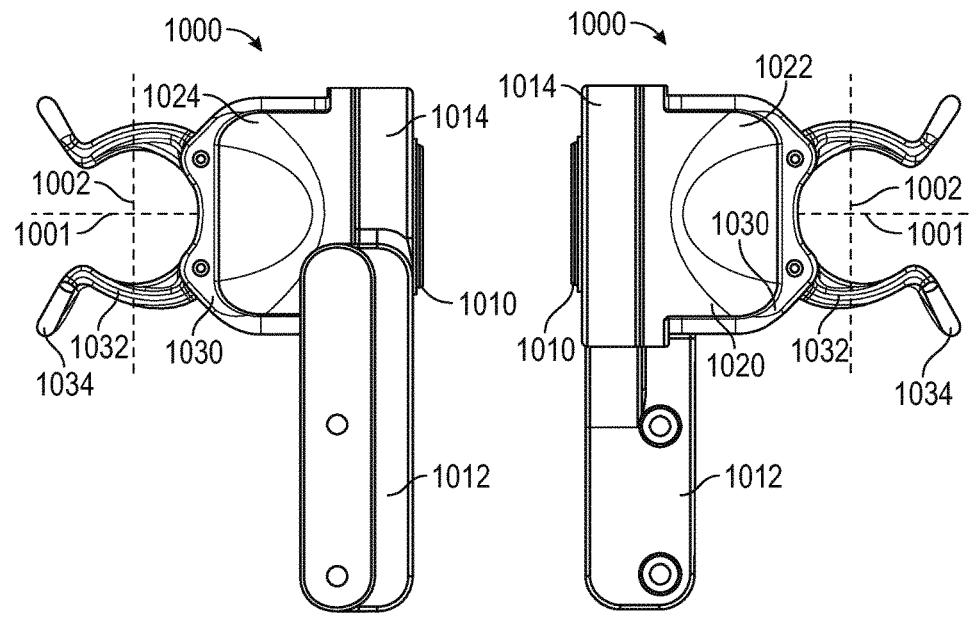
FIG. 10A shows a front view of a rotating syringe holder, in accordance with aspects of the present disclosure.
FIG. 10B shows a back view of the syringe holder of FIG. 10A, in accordance with aspects of the present disclosure.
Figures 10C, 10D:
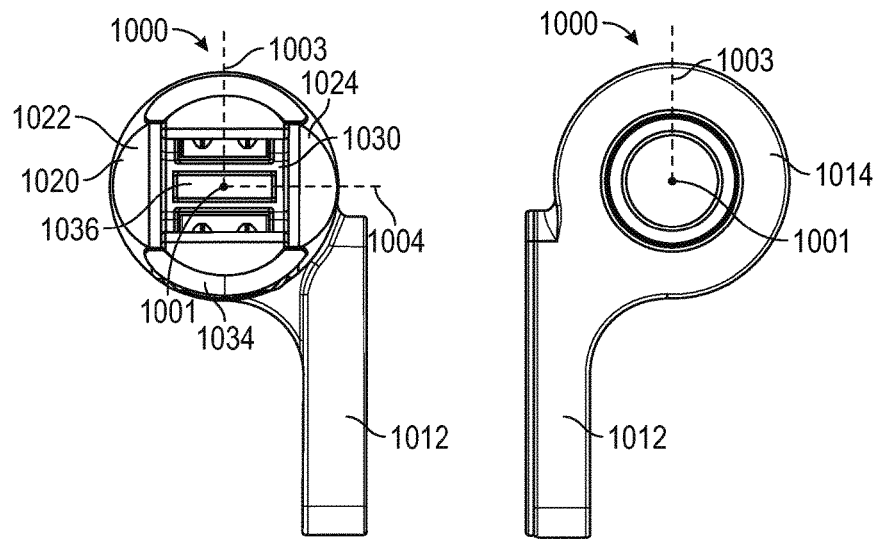
FIG. 10C shows a side view of the syringe holder of FIG. 10A, in accordance with aspects of the present disclosure.
FIG. 10D shows an opposite side view of the syringe holder of FIG. 10A, in accordance with aspects of the present disclosure.

FIGS. 10A and 10B also show a plane of rotation 1002. The plane of rotation 1002 corresponds to the plane on which the syringe remains, but pivots around the pivot axis 1001. As seen in FIGS. 10A and 10B, the plane of rotation 1002 is offset from the attachment portion 1012 such that the syringe may be rotated without interference from a surface the attachment portion 1012 attaches to. For example, if the attachment portion 1012 attaches to a fluid delivery system the plane of rotation 1002 is offset from the fluid delivery system. Although the plane of rotation 1002 may have a constant offset distance, in implementations in which the syringe clamp 1030 may move with respect to the swivel 1020, the offset distance may vary, although the offset distance will not be zero.

Figure 10E:
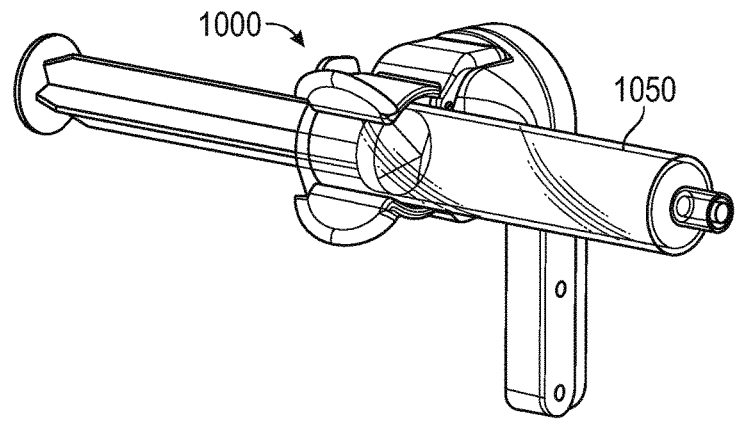
FIG. 10E shows another view of the syringe holder of FIG. 10A, holding a syringe, in accordance with aspects of the present disclosure.
Figure 10F:
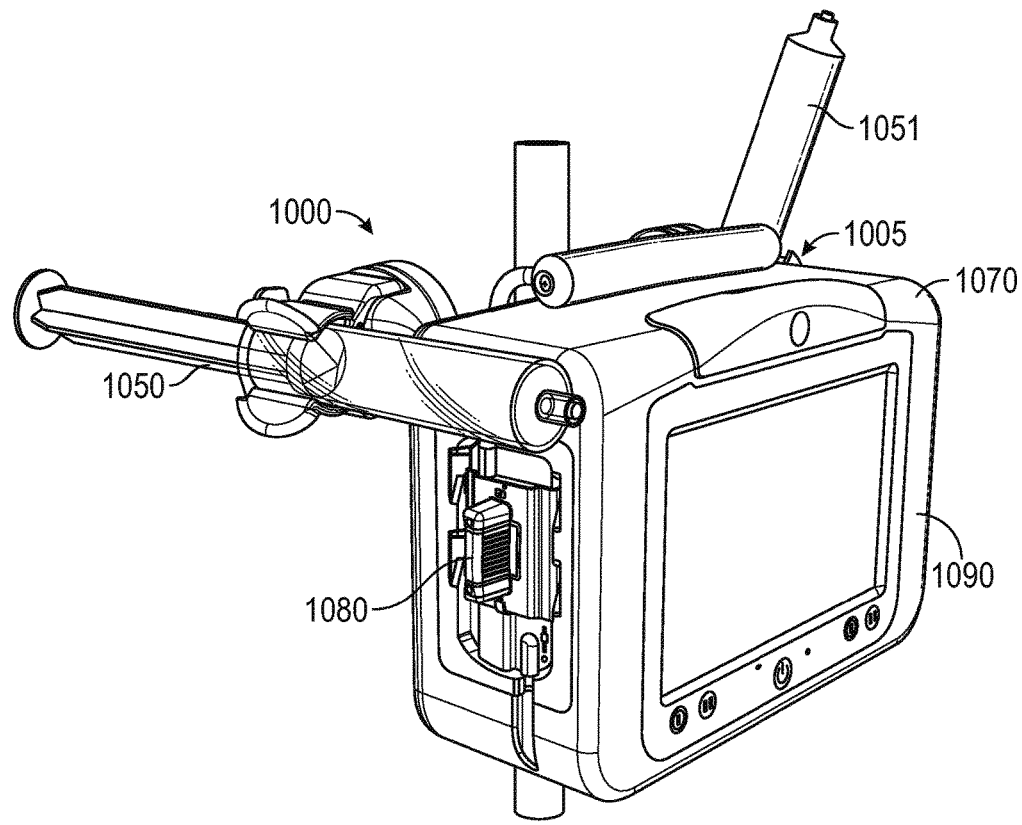
FIG. 10F shows the syringe holder of FIG. 10E attached to a fluid delivery device, in accordance with aspects of the present disclosure.
Figure 11A:
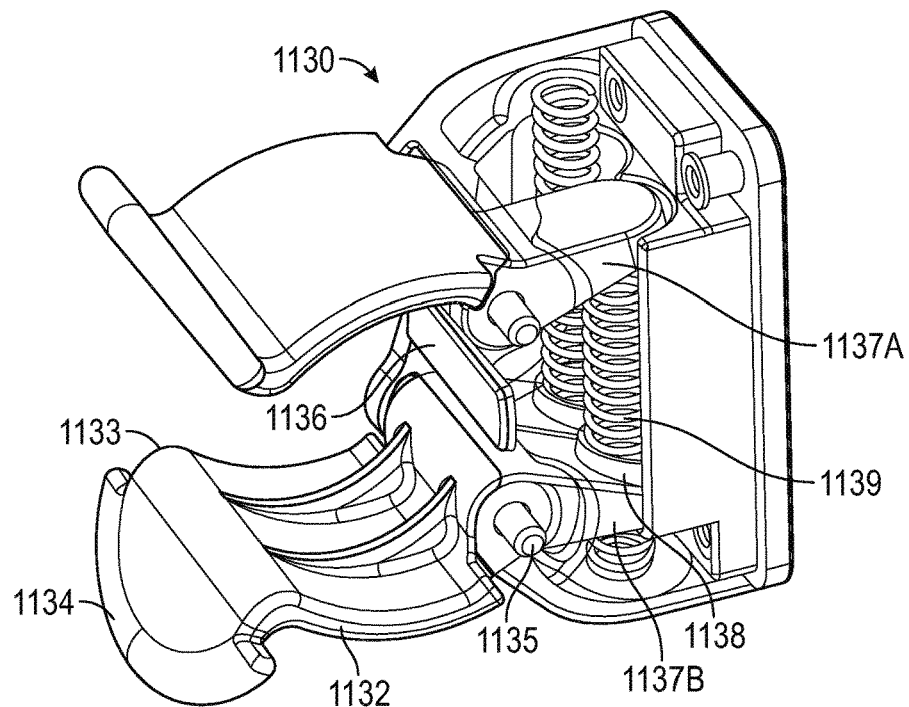
FIG. 11A shows a syringe clamp of a syringe holder, in accordance with aspects of the present disclosure.
Figure 11B:
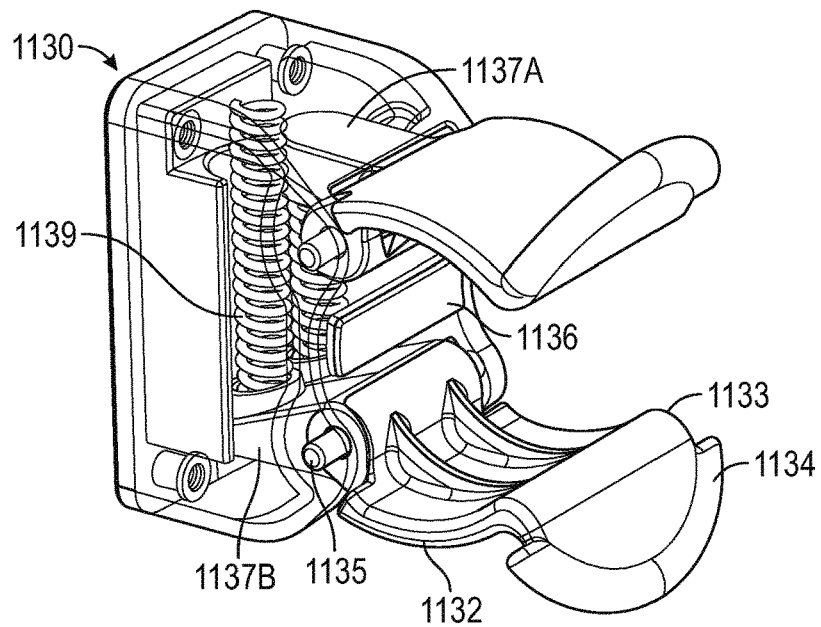
FIG. 11B shows an alternate view of the syringe clamp of FIG. 11A, in accordance with aspects of the present disclosure.

Turning to FIGS. 10E and 10F, FIGS. 10E and 10F show the syringe holder 1000 holding a syringe 1050. FIG. 10F shows the syringe holder 1000 attached to a fluid delivery system 1070. The fluid delivery system 1070 comprises a main body 1090 and a cassette 1080. The syringe holder 1000 attaches to the main body 1090 through the attachment portion 1012. For instance, the attachment portion 1012 may include holes for screws to attach the attachment portion 1012 to the main body 1090, which may include an indent corresponding to the attachment portion 1012. In other implementations, other attachment mechanisms may be used. In yet other implementations, the attachment portion 1012 may be permanently coupled to the main body 1090, or may be integrated with the main body 1090.

The syringe clamp 1030 is configured to extend away from the main body 1090 such that the plane of rotation 1002 is offset from the main body 1090. The offset allows the syringe 1050 to rotate without interference from the main body 1090 as well as other components of the fluid delivery system 1070, such as the cassette 1080. The pivoting of the syringe clamp 1030 allows for more flexibility when installing syringes onto the syringe holder 1000. For example, the barrel of the syringe may be in vertical (either tip up or down), horizontal (in either tip orientation), or other angled positions. The positions may be advantageous for certain fluids, such as horizontal for mother's milk. The pivoting may further reduce air-in-line alarms, for example by positioning the barrel downwards or horizontally. The syringe may be angled or moved to an angle that allows removal of the cassette 1080 or other connected components of the fluid delivery system 1070 without disrupting other components, such as pumps, syringes, or devices. The pivoting improves line management of IV lines connected to the syringe or components of the fluid delivery system 1070, as the syringes may be appropriately positioned to reduce or prevent tangling of IV lines. The pivoting may also allow the syringes to be positioned such that the labels and graduation marks of the syringes may be seen without removing the syringes.

FIG. 10F also shows a syringe 1051 held by a syringe holder 1005. The syringe holder 1000 may be configured to attach to one side of the main body 1090, such as the left side when facing a front of the main body 1090. The syringe holder 1005 may be configured to attach to another side, such as the right side when facing the front of the main body 1090. The syringe holder 1005 may be a mirror of the syringe holder 1000, and may resemble the syringe holder 900 in FIG. 9. For example, the pivot portion 1014 is attached to one side of the attachment portion 1012 for the syringe holder 1000, but may be attached to the other side of the attachment portion for the syringe holder 1005. However, in implementations the syringe holder 1000 may be configured to attach to either side, such as the pivot portion 1014 attached to the middle of the attachment portion 1012.

FIG. 10F also shows that the syringes 1050 and 1051 may be held at different angles. In FIG. 10F, the syringe 1050 is at 90 degrees, and the syringe 1051 is at −20 degrees. In addition, the syringe clamp arms 1032 may be colored or otherwise visibly marked to distinguish from the syringes and fluids therein.

FIGS. 11A-11G illustrate a syringe clamp 1130, which may correspond to the syringe clamp 930 or the syringe clamp 1030. The syringe clamp 1130 comprises a pad 1136 and a pair of syringe clamp arms 1132, each connected to an outward projection 1134 by a rounded corner 1133. Each syringe clamp arm 1132 is also connected to a lever portion 1137A or 1137B, and is configured to pivot about a pivot point 1135, which may be a pin. Springs 1139 may be configured to push outwards against the lever portions 1137A and 1137B such that the syringe clamp arms 1132 pivot about the pivot point 1135 such that the syringe clamp arms 1132 are held together in the closed position when no syringe is inserted.

For example, FIG. 11C shows the syringe clamp arms 1132 in the closed position when a large syringe 1150 is not inserted. The lever portion 1137A is approximately half a width of the syringe clamp arm 1132 such that the lever portion 1137A engages one spring 1139 without interfering with the spring 1139 engaging the opposite lever portion 1137B. The lever portion 1137B is approximately the width of the syringe clamp arm 1132 and may include a hole 1138 for allowing one spring 1139 through such that the lever portion 1137B engages one spring 1139. In other implementations, the hole 1138 may not be included such that the lever portion 1137B engages more than one spring 1139. In other implementations, other resistive mechanisms may be used to hold the syringe clamp arms 1132 in the closed position.

The syringe clamp 1130 is configured to hold syringes of various sizes. The large syringe 1150 has a diameter greater than a diameter of a small syringe 1160. The large syringe 1150 may correspond to a 60 cc syringe and the small syringe 1160 may correspond to a 20 cc syringe, although the volumes may be different. FIGS. 11C-11E show installation of the large syringe 1150 into the syringe clamp 1130. In FIG. 11C, the large syringe 1150 is pushed against the outward projections 1134 and the rounded corners 1133, which pushes the syringe clamp arms 1132 outward and the lever portions 1137 inward against the springs 1139. The shape of the syringe clamp arms 1132 may reduce friction to allow pushing the large syringe 1150 against the syringe clamp arms 1132 to open the syringe clamp arms 1132. The shape of the syringe clamp arms 1132 may further allow off-axis installation of the large syringe 1150 such that the large syringe 1150 is not required to align with the zero degree heading of the syringe clamp 1130.

In FIG. 11D, the large syringe 1150 is pushed further into the syringe clamp 1130, and as it passes the rounded corners 1133, the syringe arms 1132 start to close around the large syringe 1150. In FIG. 11E, the large syringe 1150 is pushed up against the pad 1136 and an inner wall 1131 of the syringe clamp 1130. The pad 1136 may provide grip and cushioning for the large syringe 1150. The inner wall 1131 may be curved to better conform to the circular shape of the large syringe 1150. Extraction of the large syringe 1150 may follow a reverse order, by pushing against the rounded corners 1133 to open the syringe arms 1132. In addition, the syringe clamp 1130 may be configured to allow single-handed installation of syringes. For instance, the shape of the syringe clamp arms 1132 (which include the outward projections 1134 and rounded corners 1133), and the springs 1139 may allow installation without requiring a large force. Similarly, extraction of the syringes may not require large force.

FIGS. 11F-11G show the small syringe 1160 inserted into the syringe clamp 1130, which may be inserted in a similar process as described with respect to the large syringe 1150 in FIGS. 11C-11E. Due to the smaller diameter of the small syringe 1160, the syringe clamp arms 1132 may be closer together than when the large syringe 1150 is inserted, as seen in FIGS. 11E and 11G.

The springs 1139 may be modified based on required installation forces. For instance, the syringe clamp 1130 may utilize compression, torsional, or formed spring steel to modify the installation force, or may utilize a permanent flexure member for a push type clamp.

Figure 12B:
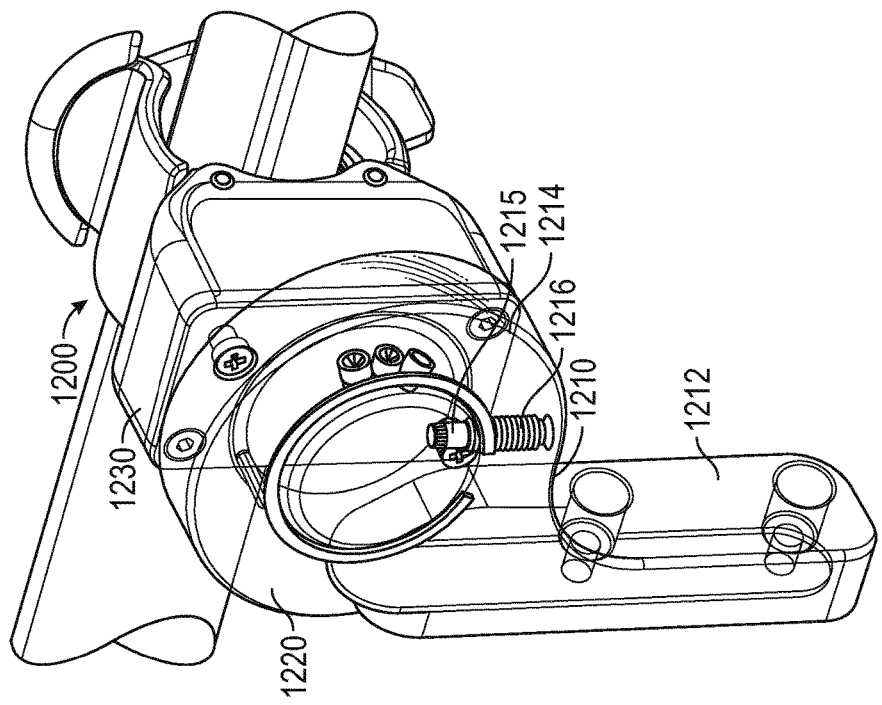
FIG. 12B shows an alternate view of the base of FIG. 12A, in accordance with aspects of the present disclosure.
Figure 12A:
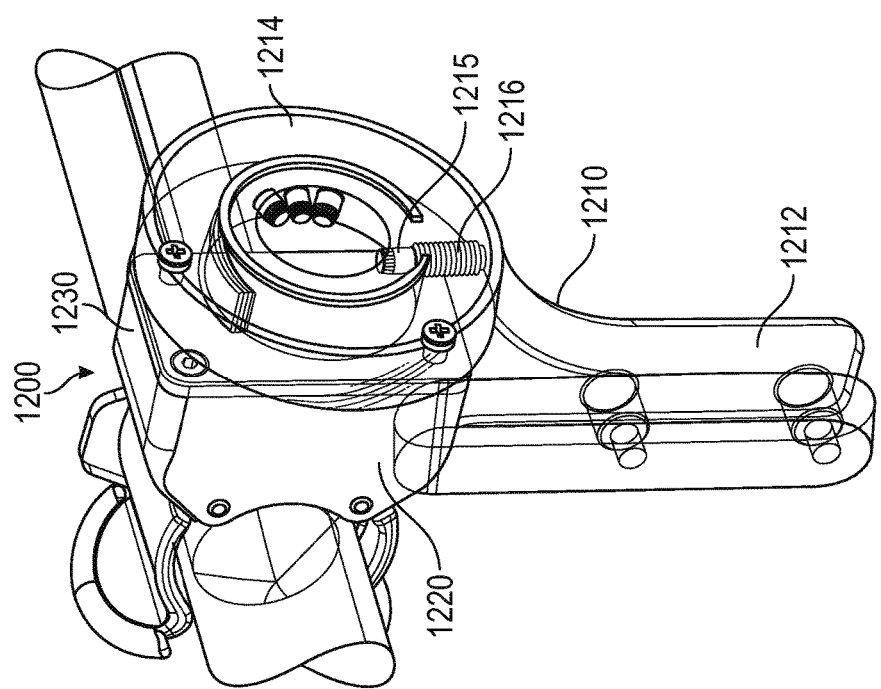
FIG. 12A shows a base of a syringe holder, in accordance with aspects of the present disclosure.

FIGS. 12A and 12B show a syringe holder 1200, which may correspond to the syringe holders 900, 1000, and/or 1100. The syringe holder 1200 comprises a base 1210 comprising an attachment portion 1212 and a pivot portion 1214. The syringe holder 1200 also comprises a swivel 1220 and a syringe clamp 1230. The swivel 1220 comprises one or more detents 1215. The pivot portion 1214 comprises a detent mechanism 1216, which may comprises a spring and a detent pin configured to lock into one of the detents 1215. As the swivel 1220 rotates, the detents 1215 move radially. If one of the detents 1215 is aligned with the detent mechanism 1216, the detent mechanism 1216 locks into the detent 1215. When the detent mechanism 1216 is locked into the detent 1215, the syringe holder 1200 holds a syringe at a detent angle corresponding to the detent 1215. The detent angle may be defined with respect to the zero degree heading as described herein. The detents 1215 may be located at various detent angles, such as −20, 0, +20, and 90 degrees. Rotating the swivel 1220 out of a detent angle may require more force than rotating the swivel 1220 without the detent mechanism 1216 locked such that the swivel 1220 will not move from the force of gravity. In other words, a force must be applied to move the swivel 1220 out of a detent angle.

In addition, the detent mechanism 1216 may comprise an audible indicator such that an audible signal may be heard when the detent mechanism 1216 locks into one of the detents 1215. In implementations, the audible indicator may be the detent mechanism 1216, where the mechanical action of the detent mechanism 1216 into the detent 1215 produces an audible sound. In other implementations, the detent mechanism 1216 and the detents 1215 may comprise electrical contacts such that a signal may be sent to an audio device when the detent mechanism 1216 locks into the detent 1215. The syringe holder 1200 may also include electrical contacts for coupling to electrical contacts on a fluid delivery system such that the signal is sent to the fluid delivery system. For instance, a screen of the fluid delivery system may be able to display a status, such as the current heading, of the syringe holder 1200 based on the signals. In implementations, the pivot portion 1214 and/or the swivel 1220 may include visible indicators corresponding to the detent angles. For example, the swivel 1220 may include a marking corresponding to the zero degree heading, and the pivot portion 1214 may include markings at each detent angle.

Figure 13B:
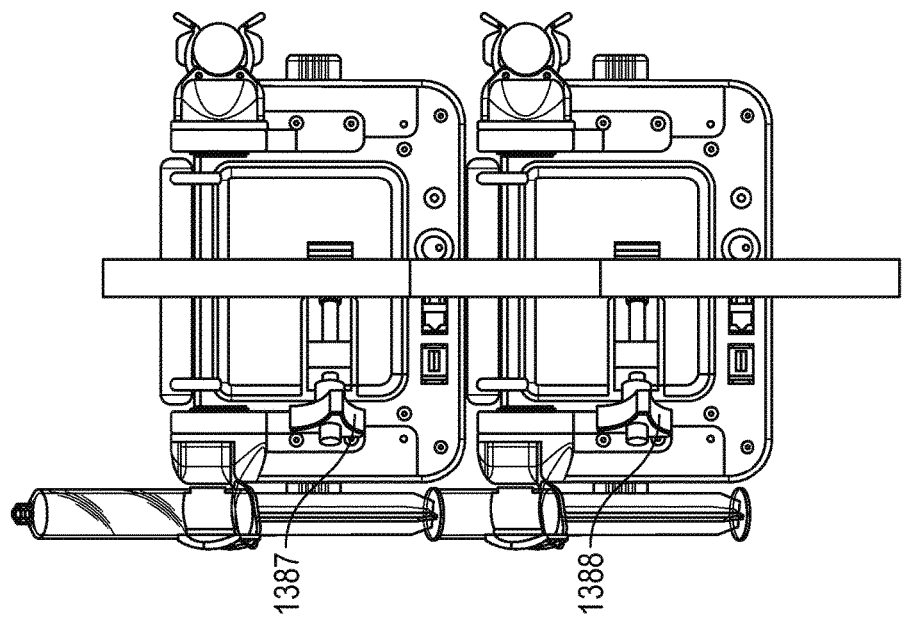
FIG. 13B shows a back view of the fluid delivery system of FIG. 13A, in accordance with aspects of the present disclosure.
Figure 13A:
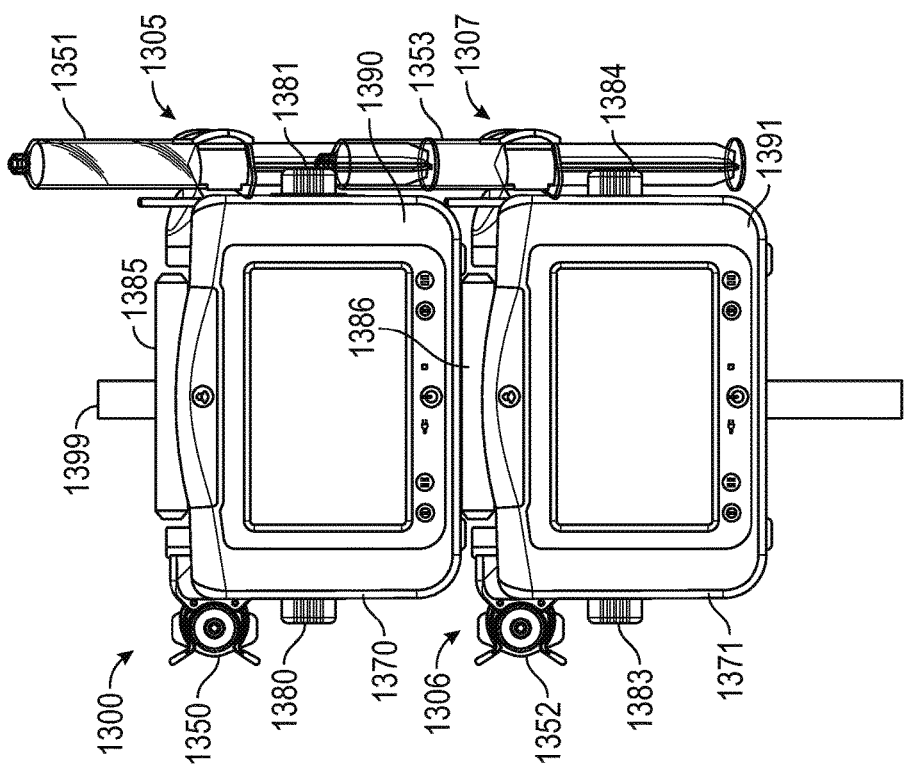
FIG. 13A shows a front view a fluid delivery system with syringe holders, in accordance with aspects of the present disclosure.

FIGS. 13A-13E show multiple fluid delivery systems nested on a pole 1399. A first fluid delivery system 1370 comprises a first main body 1390, a cassette 1380, a cassette 1381, a syringe holder 1300, a syringe holder 1305, a bumper 1385, and a pole clamp 1387. The syringe holder 1300 holds a syringe 1350 and the syringe holder 1305 holds a syringe 1351. A second fluid delivery system 1371 comprises a second main body 1391, a cassette 1383, a cassette 1384, a syringe holder 1306, a syringe holder 1307, a bumper 1386, and a pole clamp 1388. The syringe holder 1306 holds a syringe 1352 and the syringe holder 1307 holds a syringe 1353. The pole clamps 1387 and 1388 are configured to hold the fluid delivery systems 1370 and 1371, respectively to the pole 1399. FIG. 13A shows a front view of the fluid delivery systems 1370 and 1371 on the pole 1399, FIG. 13B shows a back view, FIG. 13C shows a left side view, and FIG. 13D shows a right side view. As seen in FIGS. 13C and 13D, the pivoting of the syringe holders 1300, 1305, 1306, and 1307 allow the syringes 1350, 1351, 1352, and 1353 to be positioned to not interfere with access to the cassettes 1380, 1381, 1382, and 1383. In addition, an offset space may be defined between the syringes of the nested fluid delivery systems. For example, there is an offset space between the syringes 1350 and 1352 in FIG. 13C, and an offset space between the syringes 1351 and 1353 in FIG. 13D. In FIGS. 13C and 13D, the syringes 1350 and 1352 and the syringes 1352 and 1353 may be positioned at the same detent angles, however other detent angles may be used to define the respective offset spaces. The offset spaces may reduce or prevent tangling of IV lines, or other interference between components, and may further allow a fluid delivery system to be removed from the pole 1399 without disrupting the other fluid delivery systems on the pole 1399.

The fluid delivery systems 1370 and 1371 include the bumpers 1385 and 1386, respectively. The bumpers 1385 and 1386 are configured to offset the main bodies of the fluid delivery systems. For example, the bumper 1386 offsets the first main body 1390 from the second main body 1391 such that the first main body 190 does not interfere with the second main body 1391. The bumpers 1385 and 1386 may comprise a soft material to cushion the main bodies. The offset from the bumper, and/or the offset spaces from the rotated syringes may increase a number of fluid delivery systems nested on the pole 1399 by reducing the possibility of tangling or other interference between components of the nested fluid delivery systems.

FIG. 13E shows four fluid delivery systems, the fluid delivery system 1370, the fluid delivery system 1371, a fluid delivery system 1372, and a fluid delivery system 1373, nested on the pole 1399. The syringe holders of each respective fluid delivery system may be positioned independent of the other syringe holders as needed. Although FIG. 13E shows four nested fluid delivery systems, in other implementations more or less fluid delivery systems may be nested.

It is understood that any specific order or hierarchy of blocks in the processes disclosed is an illustration of example approaches. Based upon design or implementation preferences, it is understood that the specific order or hierarchy of blocks in the processes may be rearranged, or that all illustrated blocks may or may not be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed provide exemplary approaches. Based upon implementation specifics or preferences, it is understood that the specific order or hierarchy of steps, operations or processes may be rearranged. Some of the steps, operations or processes may be performed simultaneously and some may be omitted. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A syringe holder for housing a syringe, the syringe holder comprising:
a base comprising an attachment portion and a pivot portion defining a pivot axis, wherein the attachment portion is configured to fixedly attach the base to a main body of an infusion device that includes a mechanism for pumping fluid from the syringe;
a syringe clamp configured to hold a syringe transversely to the pivot axis, wherein the pivot axis extends through the syringe clamp; and
a swivel configured to couple with the base and the syringe clamp, wherein the swivel and syringe clamp are rotatable, relative to the base, about the pivot axis to allow rotation of the syringe relative to the main body of the infusion device,
wherein the swivel comprises a first portion and a second portion defining a cavity between the first portion and the second portion for receiving the syringe clamp,
wherein the syringe clamp further comprises a pad configured to restrict the syringe from sliding and to provide cushion against the syringe clamp for the syringe.

2. The syringe holder of claim 1, wherein the syringe clamp is configured to hold the syringe perpendicular to the pivot axis.

3. The syringe holder of claim 1, wherein the syringe clamp comprises a syringe clamp arm configured to move between an open position and a closed position.

4. The syringe holder of claim 3, wherein the syringe clamp arm is configured to move to the closed position by a spring mechanism.

5. The syringe holder of claim 3, wherein the syringe clamp arm comprises an outward-projecting portion.

6. The syringe holder of claim 1, wherein the swivel is configured to freely rotate.

7. The syringe holder of claim 1, wherein the swivel is configured to rotate between a first angle about the pivot axis and a second angle about the pivot axis.

8. The syringe holder of claim 1, wherein the pivot portion comprises a first detent mechanism configured to lock the swivel at a first detent angle about the pivot axis.

9. The syringe holder of claim 8, wherein the first detent mechanism comprises an audible indicator.

10. The syringe holder of claim 1, wherein the syringe clamp is disposed away from the main body, such that the pivot axis does not extend through the main body.

11. The syringe holder of claim 1, wherein the pivot axis extends through a space bounded by the syringe clamp on opposing sides of the space.

12. A fluid delivery system comprising:
a fluid delivery device comprising a main body;
a base comprising:
an attachment portion fixedly connected to the main body, and
a pivot portion defining a pivot axis;
a syringe clamp configured to hold a syringe transversely to the pivot axis, wherein the pivot axis extends through the syringe clamp; and
a swivel coupled between the base and the syringe clamp, wherein the swivel and syringe clamp are rotatable, relative to the base, about the pivot axis, to allow rotation of the syringe relative to the main body,
wherein the swivel comprises a first portion and a second portion defining a cavity between the first portion and the second portion for receiving the syringe clamp,
wherein the syringe clamp further comprises a pad configured to restrict the syringe from sliding and to provide cushion against the syringe clamp for the syringe.

13. The fluid delivery system of claim 12, wherein the syringe clamp comprises a pair of syringe clamp arms configured to move together in a closed position and move apart in an open position.

14. The fluid delivery system of claim 13, wherein each of the pair of syringe clamp arms is configured to move to the closed position by a respective spring mechanism.

15. The fluid delivery system of claim 12, wherein the pivot portion comprises a detent mechanism configured to lock the swivel at one of a plurality of detent angles about the pivot axis.

16. The fluid delivery system of claim 12, wherein the syringe clamp is configured to extend away from the main body.

17. The fluid delivery system of claim 14, wherein the syringe clamp is configured to extend away from the main body such that a plane of rotation of the syringe clamp is offset from the main body.

18. The fluid delivery system of claim 12, wherein the syringe clamp is disposed away from the main body, such that the pivot axis does not extend through the main body.

19. A fluid delivery system comprising:
a first fluid delivery device comprising a first main body;
a first base comprising:
a first attachment portion fixedly connected to the first main body, and
a first pivot portion defining a first pivot axis;
a first syringe clamp comprising a first syringe clamp arm configured to hold a first syringe transversely to the first pivot axis, wherein the first pivot axis extends through the first syringe clamp;
a first swivel coupled between the first base and the first syringe clamp, wherein the first swivel and the first syringe clamp are rotatable, relative to the first base, about the first pivot axis, to allow rotation of the first syringe relative to the first main body,
wherein the first swivel comprises a first portion and a second portion defining a first cavity between the first portion and the second portion for receiving the first syringe clamp;
wherein the first syringe clamp further comprises a first pad configured to restrict the first syringe from sliding and to provide cushion against the first syringe clamp for the first syringe;
a second fluid delivery device comprising a second main body;
a second base comprising:
a second attachment portion fixedly connected to the second main body,
and a second pivot portion defining a second pivot axis;
a second syringe clamp comprising a second syringe clamp arm configured to hold a second syringe transversely to the second pivot axis, wherein the second pivot axis extends through the second syringe clamp; and
a second swivel configured to couple with the second base and the second syringe clamp, wherein the second swivel and the second syringe clamp are rotatable, relative to the second base, about the second pivot axis, to allow rotation of the second syringe relative to the second main body and relative to the first syringe,
wherein the second swivel comprises a third portion and a fourth portion defining a second cavity between the third portion and the fourth portion for receiving the second syringe clamp, the second syringe clamp configured to pivot about the second pivot axis with the second swivel,
wherein the second syringe clamp further comprises a second pad configured to restrict the second syringe from sliding and to provide cushion against the second syringe clamp for the second syringe.

20. The fluid delivery system of claim 19, wherein the first pivot portion comprises a first detent mechanism configured to lock the first swivel at one of a first plurality of detent angles about the first pivot axis, and the second pivot portion comprises a second detent mechanism configured to lock the second swivel at one of a second plurality of detent angles about the second pivot axis.

21. The fluid delivery system of claim 20, wherein when the first syringe is held by the first syringe clamp at one of the first plurality of detent angles and when the second syringe is held by the second syringe clamp at one of the second plurality of detent angles, an offset space is defined between the first syringe and the second syringe.

22. The fluid delivery system of claim 19, wherein the second main body comprises a bumper configured to offset the first main body from the second main body.

23. The fluid delivery system of claim 19, wherein the first syringe clamp is disposed away from the first main body, such that the first pivot axis does not extend through the first main body, wherein the second syringe clamp is disposed away from the second main body, such that the second pivot axis does not extend through the second main body.

24. The fluid delivery system of claim 19, wherein the first pivot axis extends through a first space bounded by the first syringe clamp on opposing sides of the first space, and wherein the second pivot axis extends through a second space bounded by the second syringe clamp on opposing sides of the second space.

* * * * *

UNITED STATES PATENT AND TRADEMARK OFFICE
CERTIFICATE OF CORRECTION

PATENT NO. : 10,238,790 B2
APPLICATION NO. : 14/641228
DATED : March 26, 2019
INVENTOR(S) : Daniel Toro et al.

Page 1 of 1

It is certified that error appears in the above-identified patent and that said Letters Patent is hereby corrected as shown below:

In the Claims

In Column 23, Line 4:
Replace "delivery system of claim 14", with --delivery system of claim 16--.

Signed and Sealed this
Seventh Day of May, 2019

Andrei Iancu
*Director of the United States Patent and Trademark Office*